(12) United States Patent
McNichols et al.

(10) Patent No.: US 7,810,743 B2
(45) Date of Patent: *Oct. 12, 2010

(54) ULTRASONIC LIQUID DELIVERY DEVICE

(75) Inventors: Patrick Sean McNichols, Hortonville, WI (US); Thomas David Ehlert, Neenah, WI (US); Robert Allen Janssen, Alpharetta, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 266 days.

This patent is subject to a terminal disclaimer.

(21) Appl. No.: 11/780,860

(22) Filed: Jul. 20, 2007

(65) Prior Publication Data
US 2008/0006714 A1 Jan. 10, 2008

Related U.S. Application Data

(63) Continuation-in-part of application No. 11/530,311, filed on Sep. 8, 2006, now Pat. No. 7,703,698, and a continuation-in-part of application No. 11/337,634, filed on Jan. 23, 2006, now Pat. No. 7,735,751.

(51) Int. Cl.
B05B 1/08 (2006.01)
B05B 3/04 (2006.01)

(52) U.S. Cl. .............. 239/102.2; 239/584; 251/129.06; 123/498; 123/445

(58) Field of Classification Search .............. 239/102.1, 239/102.2; 251/129.06
See application file for complete search history.

(56) References Cited

U.S. PATENT DOCUMENTS

| 2,584,053 A | 1/1952 | Seavey et al. |
| 2,946,981 A | 7/1960 | O'Neill |
| 3,246,881 A | 4/1966 | Davidson et al. |
| 3,519,251 A | 7/1970 | Hammitt et al. |

(Continued)

FOREIGN PATENT DOCUMENTS

CH 657067 8/1986

(Continued)

OTHER PUBLICATIONS

Non-final office action regarding U.S. Appl. No. 11/337,638, dated Nov. 14, 2008.

(Continued)

*Primary Examiner*—Dinh Q Nguyen
(74) *Attorney, Agent, or Firm*—Armstrong Teasdale, LLP

(57) ABSTRACT

An ultrasonic liquid delivery device has an elongate housing with an internal chamber, an inlet in fluid communication with the internal chamber of the housing, and an outlet in fluid communication with the internal chamber of the housing. An elongate ultrasonic waveguide is disposed at least in part within the internal chamber of the housing to ultrasonically energize liquid within the internal chamber prior to the liquid being exhausted from the housing through the outlet. The ultrasonic waveguide has an agitating member extending outward from the ultrasonic waveguide within the internal chamber of the housing intermediate the inlet and the outlet. The agitating member and the ultrasonic waveguide are constructed and arranged for dynamic motion of the agitating member relative to the ultrasonic waveguide upon ultrasonic vibration of the ultrasonic waveguide. An excitation device is operable to ultrasonically excite the ultrasonic waveguide and the agitating member.

21 Claims, 15 Drawing Sheets

U.S. PATENT DOCUMENTS

| | | |
|---|---|---|
| 3,542,345 A | 11/1970 | Kuris |
| 3,567,185 A | 3/1971 | Ross et al. |
| 3,865,350 A | 2/1975 | Burtis |
| 4,259,021 A | 3/1981 | Goudy, Jr. |
| 4,266,879 A | 5/1981 | McFall |
| 4,389,999 A | 6/1983 | Jaqua |
| 4,469,974 A | 9/1984 | Speranza |
| 4,511,254 A | 4/1985 | North et al. |
| 4,535,741 A | 8/1985 | Hertz |
| 4,750,706 A | 6/1988 | Schlagmuller |
| 4,764,021 A * | 8/1988 | Eppes ................. 366/127 |
| 4,799,622 A | 1/1989 | Ishikawa et al. |
| 4,974,780 A | 12/1990 | Nakamura et al. |
| 4,978,067 A | 12/1990 | Berger et al. |
| 4,983,045 A * | 1/1991 | Taniguchi ............... 366/117 |
| 5,026,167 A | 6/1991 | Berliner, III |
| 5,032,027 A | 7/1991 | Berliner, III |
| 5,128,193 A | 7/1992 | Anapol et al. |
| 5,169,067 A | 12/1992 | Matsusaka et al. |
| 5,248,087 A | 9/1993 | Dressler |
| 5,326,164 A | 7/1994 | Logan |
| 5,330,100 A | 7/1994 | Malinowski |
| 5,371,429 A * | 12/1994 | Manna ................. 310/328 |
| 5,391,000 A | 2/1995 | Taniguchi |
| 5,484,104 A | 1/1996 | Kukler |
| 5,516,043 A | 5/1996 | Manna et al. |
| 5,532,539 A | 7/1996 | Hielscher |
| 5,803,106 A | 9/1998 | Cohen et al. |
| 5,810,255 A | 9/1998 | Itoh et al. |
| 5,868,153 A | 2/1999 | Cohen et al. |
| 6,053,424 A | 4/2000 | Gipson et al. |
| 6,074,466 A | 6/2000 | Iwasa |
| 6,380,264 B1 | 4/2002 | Jameson et al. |
| 6,383,301 B1 | 5/2002 | Bell et al. |
| 6,450,417 B1 | 9/2002 | Gipson et al. |
| 6,488,670 B1 | 12/2002 | Schild et al. |
| 6,506,584 B1 | 1/2003 | Chandler et al. |
| 6,543,700 B2 * | 4/2003 | Jameson et al. .......... 239/102.1 |
| 6,655,826 B1 | 12/2003 | Leanos |
| 6,659,365 B2 | 12/2003 | Gipson et al. |
| 6,676,003 B2 | 1/2004 | Ehlert et al. |
| 6,688,579 B2 | 2/2004 | Grytz |
| 6,732,720 B2 | 5/2004 | Kelemencky |
| 6,772,963 B2 | 8/2004 | Neretti et al. |
| 6,827,332 B2 | 12/2004 | Hanneke et al. |
| 6,874,706 B2 | 4/2005 | Hanneke et al. |
| 6,880,770 B2 | 4/2005 | Jameson et al. |
| 6,935,770 B2 | 8/2005 | Schueler |
| 7,424,883 B2 | 9/2008 | McNichols et al. |
| 2002/0070298 A1 | 6/2002 | Jameson et al. |
| 2003/0066899 A1 | 4/2003 | Gipson |
| 2004/0022695 A1 | 2/2004 | Simon et al. |
| 2004/0112779 A1 | 6/2004 | Arndt |
| 2006/0120212 A1 | 6/2006 | Taniguchi et al. |
| 2007/0170275 A1 | 7/2007 | Ehlert |
| 2007/0170276 A1 | 7/2007 | McNichols et al. |
| 2007/0170277 A1 | 7/2007 | Ehlert |
| 2007/0170278 A1 | 7/2007 | McNichols |

FOREIGN PATENT DOCUMENTS

| | | |
|---|---|---|
| DE | 9017338 | 3/1991 |
| DE | 9017338 | 5/1991 |
| DE | 4203729 | 8/1993 |
| DE | 19854013 | 5/2000 |
| EP | 0036617 A | 9/1981 |
| EP | 0057466 | 8/1982 |
| EP | 0347891 | 12/1989 |
| EP | 0361480 | 4/1990 |
| EP | 0648531 | 4/1995 |
| FR | 2708487 | 2/1995 |
| FR | 2751702 A | 1/1998 |
| GB | 1344635 | 1/1974 |
| JP | 57005545 A | 1/1982 |
| JP | 62070656 | 4/1987 |
| JP | 03094855 | 4/1991 |
| JP | 03222851 A | 10/1991 |
| JP | 2001017970 | 1/2001 |
| SU | 1812332 | 4/1993 |
| WO | 9600318 | 1/1996 |
| WO | 9723305 | 7/1997 |
| WO | 0029178 | 5/2000 |
| WO | 2007010166 | 1/2007 |
| WO | 2007136427 | 11/2007 |

OTHER PUBLICATIONS

Non-final office action regarding U.S. Appl. No. 11/337,634, dated Dec. 26, 2008.
Non-final office action regarding U.S. Appl. No. 11/337,953, dated Dec. 18, 2008.
Non-final Office Action regarding U.S. Appl. No. 12/170,175, dated Apr. 1, 2009.
International Search Report and Written Opinion regarding PCT/IB2008/052905, dated Mar. 27, 2009.
U.S. Appl. No. 11/780,901, filed Jul. 20, 2007.
U.S. Appl. No. 11/780,840, filed Jul. 20, 2007.
U.S. Appl. No. 11/966,530, filed Dec. 28, 2007.
International Search Report and Written Opinion regarding PCT/2007/001056, dated Feb. 13, 2008.
International Search Report and Written Opinion regarding PCT/US2007/001054, dated May 14, 2007.
International Search Report and Written Opinion regarding PCT/IB2007/053621, dated Feb. 14, 2008.
International Search Report and Written Opinion regarding PCT/IB2007/053622, dated Feb. 14, 2008.
International Search Report and Written Opinion regarding PCT/IB2008/052906, dated Apr. 22, 2009.
International Search Report and Written Opinion regarding PCT/US2007/001060, dated May 20, 2009.
Non-final Office Action regarding U.S. Appl. No. 11/337,638, dated May 19, 2009.
Non-final Office Action regarding U.S. Appl. No. 11/337,953, dated May 26, 2009.
International Search Report and Written Opinion regarding PCT/IB2008/055397, dated Jun. 22, 2009.
Non-final Office Action regarding U.S. Appl. No. 11/337,634, dated Jun. 11, 2009.
Final Office action regarding U.S. Appl. No. 11/337,953, dated Dec. 31, 2009.
Non-final Office Action regarding U.S. Appl. No. 11/780,840, dated Oct. 28, 2009.
European Search Report regarding European Application No. 09169166.7, dated Oct. 28, 2009.
Non-final Office Action regarding U.S. Appl. No. 11/780,901, dated Nov. 2, 2009.
Non-final Office action regarding U.S. Appl. No. 11/337,953, dated Apr. 13, 2010.
Final Office Action regarding U.S. Appl. No. 11/780,901, dated Apr. 29, 2010.

* cited by examiner

ULTRASONIC LIQUID DELIVERY DEVICE

CROSS REFERENCE TO RELATED APPLICATION

This patent application is a continuation-in-part patent application of U.S. patent application Ser. No. 11/337,634 filed on Jan. 23, 2006 and U.S. patent application Ser. No. 11/530,311 filed on Sep. 8, 2006. Both of these applications are incorporated herein by reference in their entirety.

FIELD OF INVENTION

This invention relates generally to liquid delivery devices for delivering an atomized spray of liquid, and more particularly to an ultrasonic liquid delivery device in which ultrasonic energy is applied to the liquid by the device prior to the liquid exiting the device.

BACKGROUND

Ultrasonic liquid delivery devices are used in various fields to energize liquid for the purpose of atomizing the liquid to provide a fine mist or spray of the liquid. For example, such devices are used as nebulizers and other drug delivery devices, molding equipment, humidifiers, fuel injection systems for engines, paint spray systems, ink delivery systems, mixing systems, homogenization systems, and the like. Such delivery devices typically comprise a housing that has a flow path through which the liquid flows in a pressurized state to at least one and sometimes a plurality of exhaust ports or orifices of the housing. The pressurized liquid is forced to exit the housing at the exhaust port(s). In some constructions, the device may include a valve member to control the flow of liquid from the device.

In some conventional ultrasonic liquid delivery devices, an ultrasonic excitation member is typically incorporated in the device, and more particularly forms the portion of the housing that defines the exhaust port(s). The excitation member is vibrated ultrasonically as liquid exits the exhaust port(s) to energize impart ultrasonic energy to the exiting liquid. The ultrasonic energy tends to atomize the liquid so that a spray of liquid droplets is delivered from the exhaust port(s). As an example, U.S. Pat. No. 5,330,100 (Malinowski) discloses a fuel injection system in which a nozzle (e.g., part of the housing) of the fuel injector is itself constructed to vibrate ultrasonically so that ultrasonic energy is imparted to the fuel as the fuel flows out through an exit orifice of the injector. In such a configuration, there is a risk that vibrating the nozzle itself will result in cavitation erosion (e.g., due to cavitation of the fuel within the exit orifice) of the nozzle at the exit orifice.

In other ultrasonic liquid delivery devices the ultrasonic excitation member may be disposed in the flow path through which liquid flows within the housing upstream of the exhaust port(s). Examples of such a device are disclosed in related U.S. Pat. No. 5,803,106 (Cohen et al.); U.S. Pat. No. 5,868,153 (Cohen et al.); U.S. Pat. No. 6,053,424 (Gipson et al.) and U.S. Pat. No. 6,380,264 (Jameson et al.), the disclosure of each of which is incorporated herein by reference. These references generally disclose a device for increasing the flow rate of a pressurized liquid through an orifice by applying ultrasonic energy to the pressurized liquid. In particular, pressurized liquid is delivered into the chamber of a housing having a die tip that includes an exit orifice (or exit orifices) through which the pressurized liquid exits the chamber.

An ultrasonic horn extends longitudinally in part within the chamber and in part outward of the chamber and has a diameter that decreases toward a tip disposed adjacent the exit orifice to amplify the ultrasonic vibration of the horn at its tip. A transducer is attached to the outer end of the horn to vibrate the horn ultrasonically. One potential disadvantage of such a device is that exposure of the various components to a high-pressure environment imparts substantial stress on the components. In particular, because part of the ultrasonic horn is immersed in the chamber and another part is not, there is a substantial pressure differential imparted to the different segments of the horn, resulting in additional stress on the horn. Moreover, such apparatus cannot readily accommodate an operating valve member, which is common in some ultrasonic liquid delivery devices to control the delivery of liquid from the device.

In still other liquid delivery devices, and in particular those that include an operating valve member to control liquid flow from the device, it is known to ultrasonically excite the valve member itself as liquid exits the device. For example, U.S. Pat. No. 6,543,700 (Jameson et al.), the disclosure of which is incorporated herein by reference, discloses a fuel injector in which a valve needle of the injector is formed at least in part of a magnetostrictive material responsive to magnetic fields changing at ultrasonic frequencies. When the valve needle is positioned to permit fuel to be exhausted from the valve body (i.e., the housing), a magnetic field changing at ultrasonic frequencies is applied to the magnetostrictive portion of the valve needle. Accordingly, the valve needle is ultrasonically excited to impart ultrasonic energy to the fuel as it exits the injector via the exit orifices.

As mentioned above, ultrasonic liquid delivery devices are used in various fields to energize various liquids. Some of these liquids are multiphase or multi-component liquids (e.g., aqueous solutions) that can undesirably separate. In one example, fuel oils can separate prior to being delivered to a combustion chamber, which can significantly decrease the efficiency of the chamber. Thus, it would be advantageous to mix the fuel oil just prior to it being delivered to the combustion chamber. Other applications besides the delivery of fuel oils suffer from this same shortcoming. Moreover, some applications require the ultrasonic liquid delivery devices span a predetermine distance to position the exit orifice in the proper location. As a result, it would be desirable to have an ultrasonic waveguide that can accommodate relatively long spans.

SUMMARY

In one embodiment, an ultrasonic liquid delivery device generally comprises an elongate housing having an internal chamber, an inlet in fluid communication with the internal chamber of the housing whereby liquid enters the internal chamber, and an outlet in fluid communication with the internal chamber of the housing whereby liquid within the chamber exits the housing. An elongate ultrasonic waveguide is disposed at least in part within the internal chamber of the housing to ultrasonically energize liquid within the internal chamber prior to the liquid being exhausted from the housing through the outlet. The ultrasonic waveguide has an agitating member extending outward from the ultrasonic waveguide within the internal chamber of the housing intermediate the inlet and the outlet. The agitating member and the ultrasonic waveguide are constructed and arranged for dynamic motion of the agitating member relative to the ultrasonic waveguide upon ultrasonic vibration of the ultrasonic waveguide. An excitation is device operable to ultrasonically excite the ultrasonic waveguide and the agitating member.

In another embodiment, an ultrasonic liquid delivery device generally comprises a housing having an inlet for receiving liquid into the housing, an outlet through which liquid exits the housing, and an internal flow path in fluid communication with the inlet and the outlet to direct the flow of liquid within the housing from the inlet to the outlet. An ultrasonic waveguide is separate from the housing, elongate, and disposed at least in part within the flow path to ultrasonically energize liquid within the flow path prior to the liquid exiting the housing through the outlet. An agitating member extends outward from the ultrasonic waveguide generally. An excitation device is operable to ultrasonically excite the ultrasonic waveguide and the agitating member.

In yet another embodiment, an ultrasonic liquid delivery device generally comprises an elongate housing having an inlet for receiving liquid into the housing, an outlet through which liquid is exhausted from the housing, and a flow path within the housing in fluid communication with the inlet and the outlet for directing the liquid to flow within the housing from the inlet to the outlet. An elongate ultrasonic waveguide is disposed at least in part within the flow path to ultrasonically energize liquid within the flow path prior to the liquid exiting the housing through the outlet. The ultrasonic waveguide has at least two wavelength segments. A plurality of agitating member extends transversely outward from the ultrasonic waveguide. The agitating member and the ultrasonic waveguide are constructed and arranged for dynamic motion of the agitating member relative to the ultrasonic waveguide upon ultrasonic vibration of the ultrasonic waveguide. An excitation device is operable to ultrasonically excite the ultrasonic waveguide and the agitating member.

BRIEF DESCRIPTION OF THE DRAWINGS

Corresponding reference characters indicate corresponding parts throughout the drawings.

DETAILED DESCRIPTION

Figure 1:
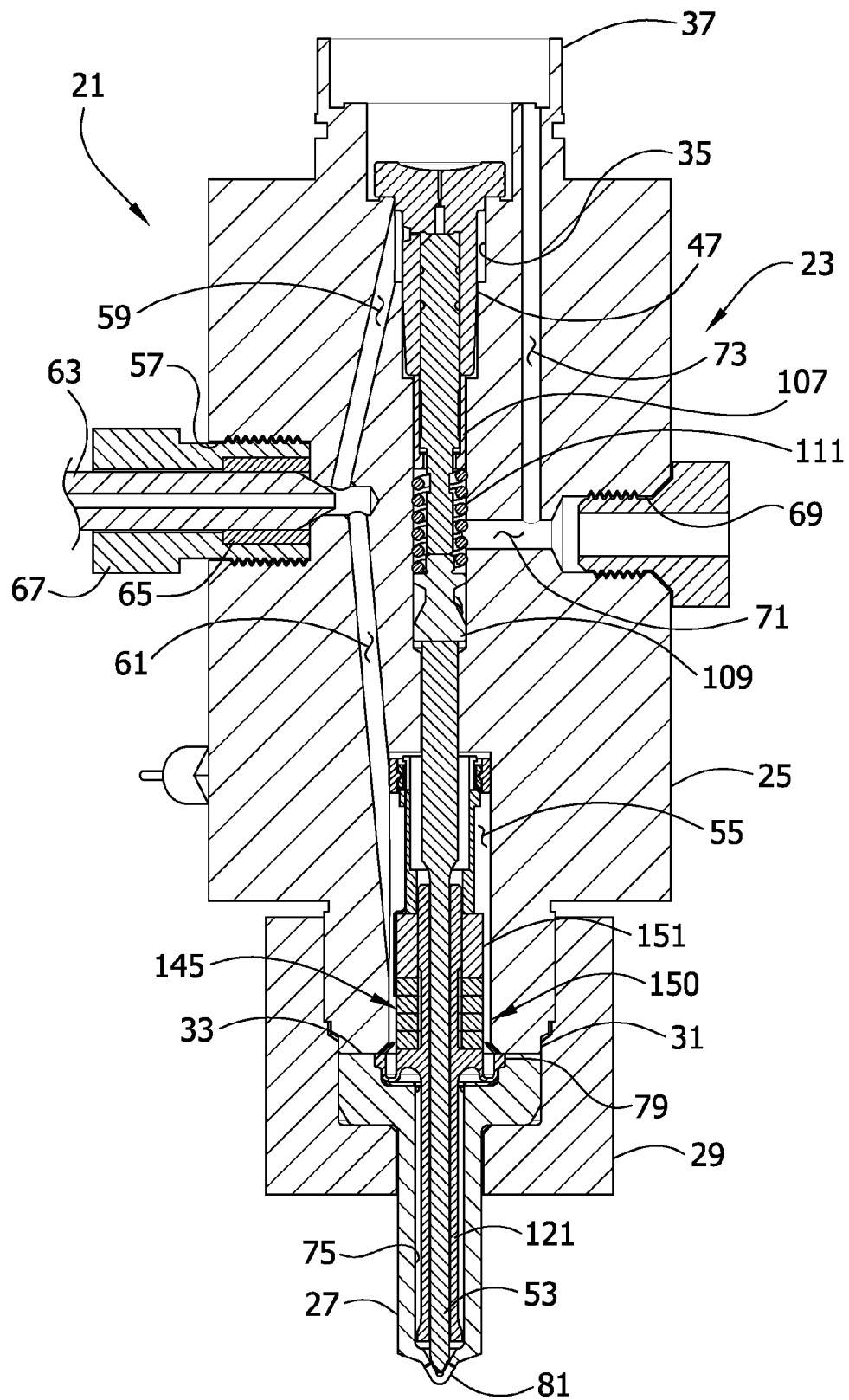
FIG. 1 is a longitudinal cross-section of one embodiment of an ultrasonic liquid delivery device of the present invention illustrated in the form of a fuel injector for delivering fuel to an internal combustion engine.

With reference now to the drawings and in particular to FIG. 1, an ultrasonic liquid delivery device according to one embodiment of the present invention is illustrated in the form of an ultrasonic fuel injector for use with an internal combustion engine (not shown) and is generally designated 21. It is understood, however, that the concepts disclosed herein in relation to the fuel injector 21 are applicable to the other ultrasonic liquid delivery devices including, without limitation, nebulizers and other drug delivery devices, molding equipment, humidifiers, paint spray systems, ink delivery systems, mixing systems, homogenization systems, and the like.

The term liquid, as used herein, refers to an amorphous (noncrystalline) form of matter intermediate between gases and solids, in which the molecules are much more highly concentrated than in gases, but much less concentrated than in solids. The liquid may comprise a single component or may be comprised of multiple components. For example, characteristic of liquids is their ability to flow as a result of an applied force. Liquids that flow immediately upon application of force and for which the rate of flow is directly proportional to the force applied are generally referred to as Newtonian liquids. Other suitable liquids have abnormal flow response when force is applied and exhibit non-Newtonian flow properties.

As examples, the ultrasonic liquid delivery device of the present invention may be used to deliver liquids such as, without limitation, molten bitumens, viscous paints, hot melt adhesives, thermoplastic materials that soften to a flowable form when exposed to heat and return to a relatively set or hardened condition upon cooling (e.g., crude rubber, wax, polyolefins and the like), syrups, heavy oils, inks, fuels, liquid medication, emulsions, slurries, suspensions and combinations thereof.

The fuel injector 21 illustrated in FIG. 1 may be used with land, air and marine vehicles, electrical power generators and other devices that employ a fuel operated engine. In particular, the fuel injector 21 is suitable for use with engines that use diesel fuel. However, it is understood that the fuel injector is useful with engines that use other types of fuel. Accordingly, the term fuel as used herein is intended to mean any combustible fuel used in the operation of an engine and is not limited to diesel fuel.

The fuel injector 21 comprises a housing, indicated generally at 23, for receiving pressurized fuel from a source (not shown) of fuel and delivering an atomized spray of fuel droplets to the engine, such as to a combustion chamber of the engine. In the illustrated embodiment, the housing 23 comprises an elongate main body 25, a nozzle 27 (sometimes also referred to as a valve body) and a retaining member 29 (e.g., a nut) holding the main body, nozzle and nut in assembly with each other. In particular, a lower end 31 of the main body 25 seats against an upper end 33 of the nozzle 27. The retaining member 29 suitably fastens (e.g., threadably fastens) to the outer surface of the main body 25 to urge the mating ends 31, 33 of the main body and nozzle 27 together.

The terms "upper" and "lower" are used herein in accordance with the vertical orientation of the fuel injector 21 illustrated in the various drawings and are not intended to describe a necessary orientation of the fuel injector in use. That is, it is understood that the fuel injector 21 may be oriented other than in the vertical orientation illustrated in the drawings and remain within the scope of this invention. The terms axial and longitudinal refer directionally herein to the lengthwise direction of the fuel injector (e.g., the vertical direction in the illustrated embodiments). The terms transverse, lateral and radial refer herein to a direction normal to the axial (e.g., longitudinal) direction. The terms inner and outer are also used in reference to a direction transverse to the axial direction of the fuel injector, with the term inner referring to a direction toward the interior of the fuel injector and the term outer referring to a direction toward the exterior of the injector.

The main body 25 has an axial bore 35 extending longitudinally along its length. The transverse, or cross-sectional dimension of the bore 35 (e.g., the diameter of the circular bore illustrated in FIG. 1) varies along discrete longitudinal segments of the bore for purposes which will become apparent. In particular, with reference to FIG. 3, at an upper end 37 of the main body 25 the cross-sectional dimension of the bore 35 is stepped to form a seat 39 for seating a conventional solenoid valve (not shown) on the main body with a portion of the solenoid valve extending down within the central bore of the main body. The fuel injector 21 and solenoid valve are held together in assembly by a suitable connector (not shown). Construction and operation of suitable solenoid valves are known to those skilled in the art and are therefore not described further herein except to the extent necessary. Examples of suitable solenoid valves are disclosed in U.S. Pat. No. 6,688,579 entitled "Solenoid Valve for Controlling a Fuel Injector of an Internal Combustion Engine," U.S. Pat. No. 6,827,332 entitled "Solenoid Valve," and U.S. Pat. No. 6,874,706 entitled "Solenoid Valve Comprising a Plug-In/Rotative Connection." Other suitable solenoid valves may also be used.

Figure 4:
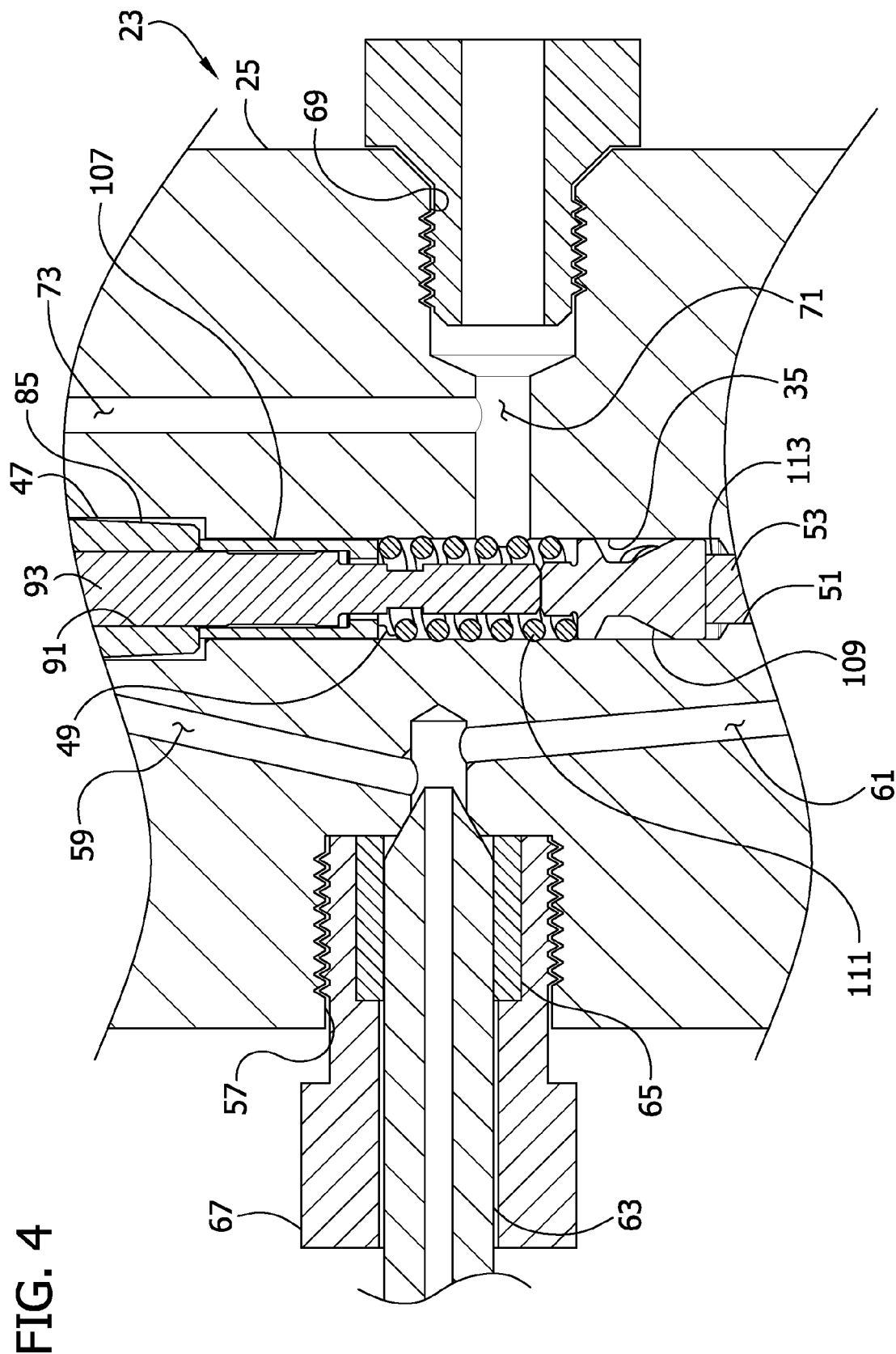
FIG. 4 is an expanded view of a second portion of the cross-section of the FIG. 1.

The cross-sectional dimension of the central bore 35 is stepped further inward as it extends below the solenoid valve seat to define a shoulder 45 which seats a pin holder 47 that extends longitudinally (and coaxially in the illustrated embodiment) within the central bore. As illustrated in FIG. 4, the bore 35 of the main body 25 further narrows in cross-section as it extends longitudinally below the segment of the bore in which the pin holder 47 extends, and defines at least in part a low pressure chamber 49 of the injector 21.

Figure 8:
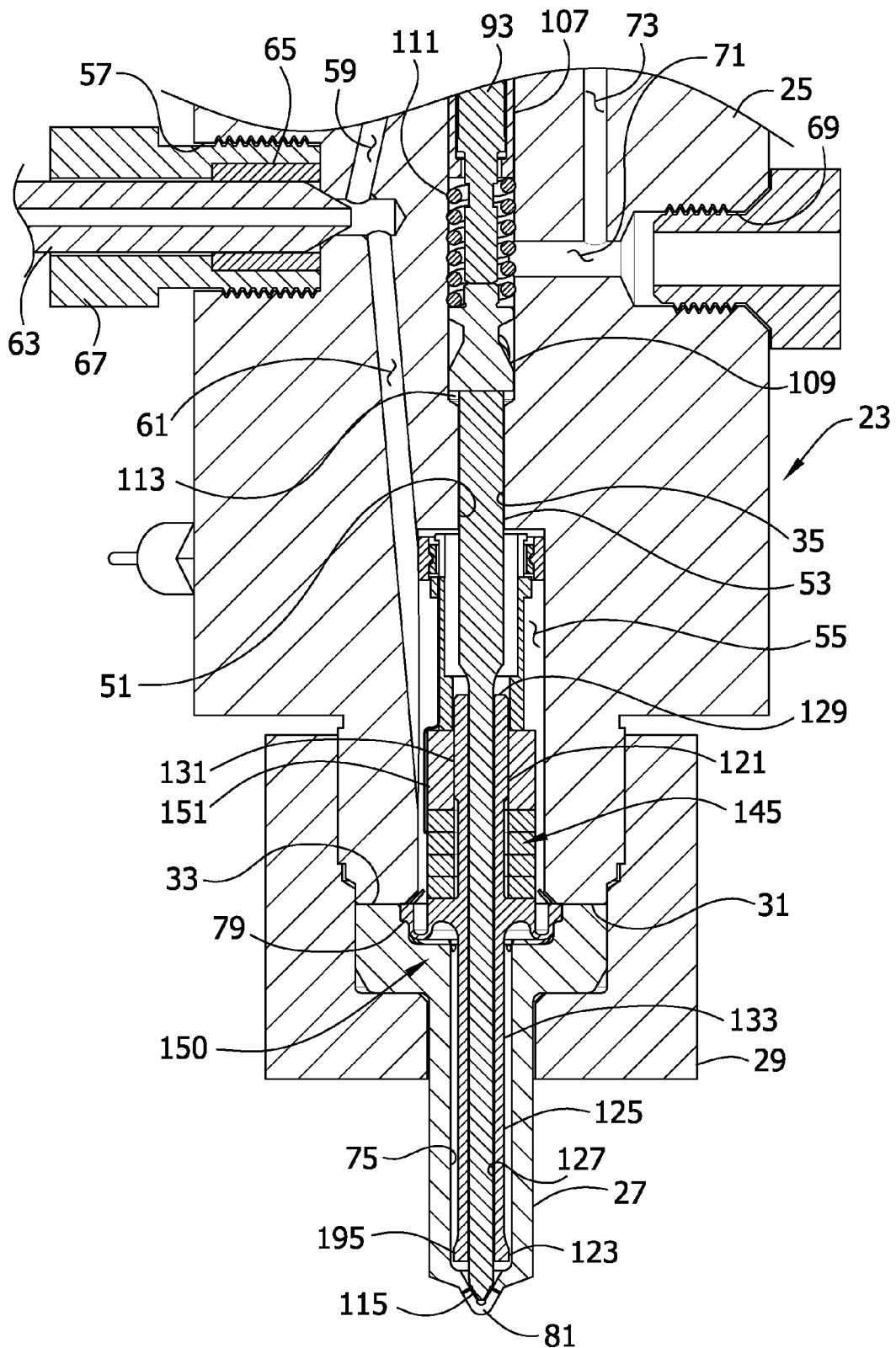
FIG. 8 is a fragmented and enlarged view of the cross-section of FIG. 1.

Longitudinally below the low pressure chamber 49, the central bore 35 of the main body 25 narrows even further to define a guide channel (and high pressure sealing) segment 51 (FIGS. 4 and 5) of the bore for at least in part properly locating a valve needle 53 (broadly, a valve member) of the injector 21 within the bore as described later herein. With reference to FIG. 8, the cross-sectional dimension of the bore 35 then increases as the bore extends longitudinally below the guide channel segment 51 to the open lower end 31 of the main body 25 to in part (e.g. together with the nozzle 27 as will be described) define a high pressure chamber 55 (broadly, an internal fuel chamber and even more broadly an internal liquid chamber) of the injector housing 23.

A fuel inlet 57 (FIGS. 1 and 4) is formed in the side of the main body 25 intermediate the upper and lower ends 37, 31 thereof and communicates with diverging upper and lower distribution channels 59, 61 extending within the main body. In particular, the upper distribution channel 59 extends from the fuel inlet 57 upward within the main body 25 and opens into the bore 35 generally adjacent the pin holder 47 secured within the bore, and more particularly just below the shoulder 45 on which the pin holder is seated. The lower distribution channel 61 extends from the fuel inlet 57 down within the main body 25 and opens into the central bore 35 generally at the high pressure chamber 55. A delivery tube 63 extends inward through the main body 25 at the fuel inlet 57 and is held in assembly with the main body by a suitable sleeve 65 and threaded fitting 67. It is understood that the fuel inlet 57 may be located other than as illustrated in FIGS. 1 and 4 without departing from the scope of the invention. It is also understood that fuel may delivered solely to the high pressure chamber 55 of the housing 23 and remain within the scope of this invention.

The main body 25 also has an outlet 69 (FIGS. 1 and 4) formed in its side through which low pressure fuel is exhausted from the injector 21 for delivery to a suitable fuel return system (not shown). A first return channel 71 is formed in the main body 25 and provides fluid communication between the outlet 69 and the low pressure chamber 49 of the central bore 35 of the main body. A second return channel 73 is formed in the main body 25 to provide fluid communication between the outlet 69 and the open upper end 37 of the main body. It is understood, however, that one or both of the return channels 71, 73 may be omitted from the fuel injector 21 without departing from the scope of this invention.

Figure 6:
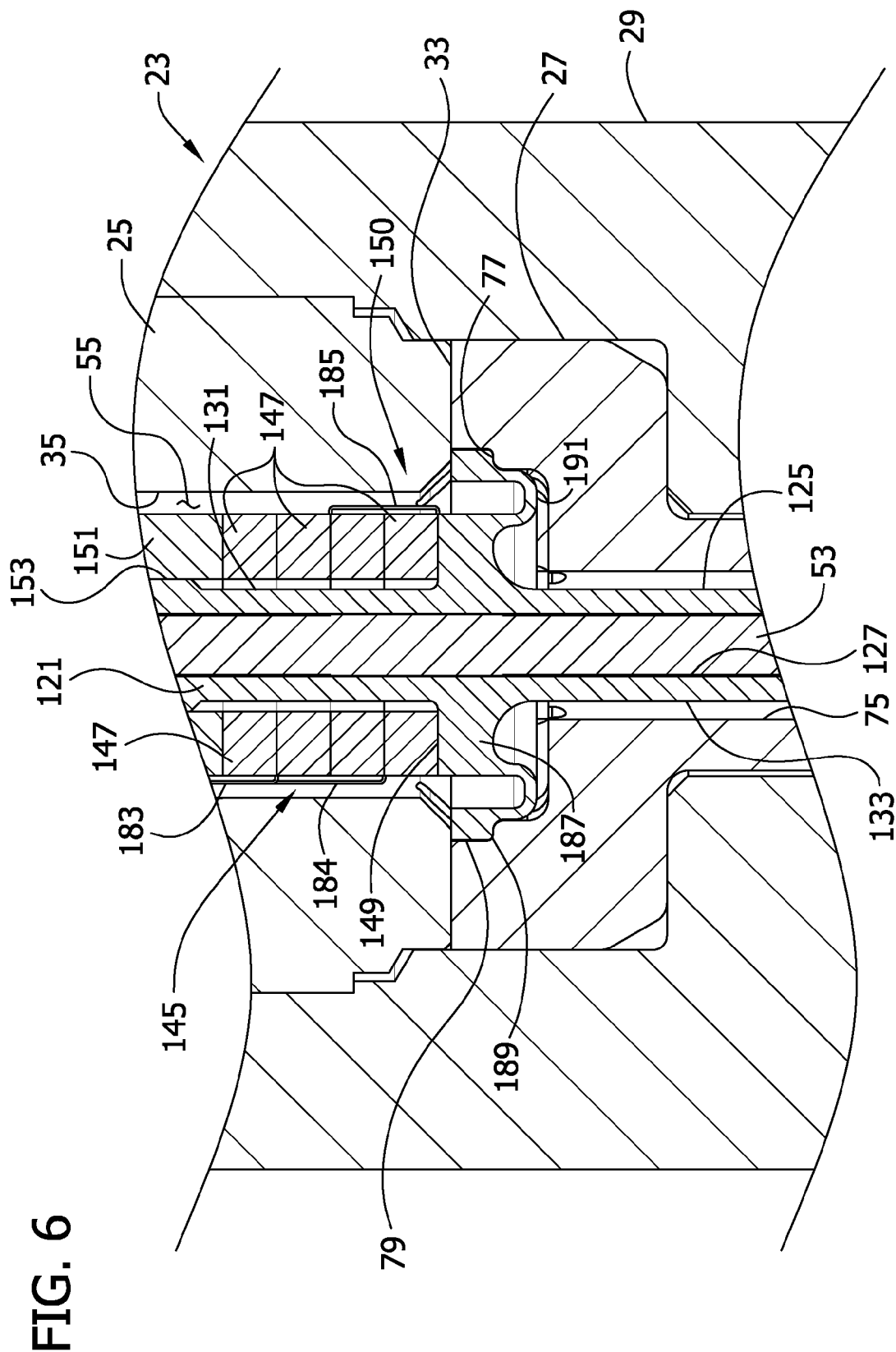
FIG. 6 is an expanded view of a fourth portion of the cross-section of FIG. 1.
Figure 7:
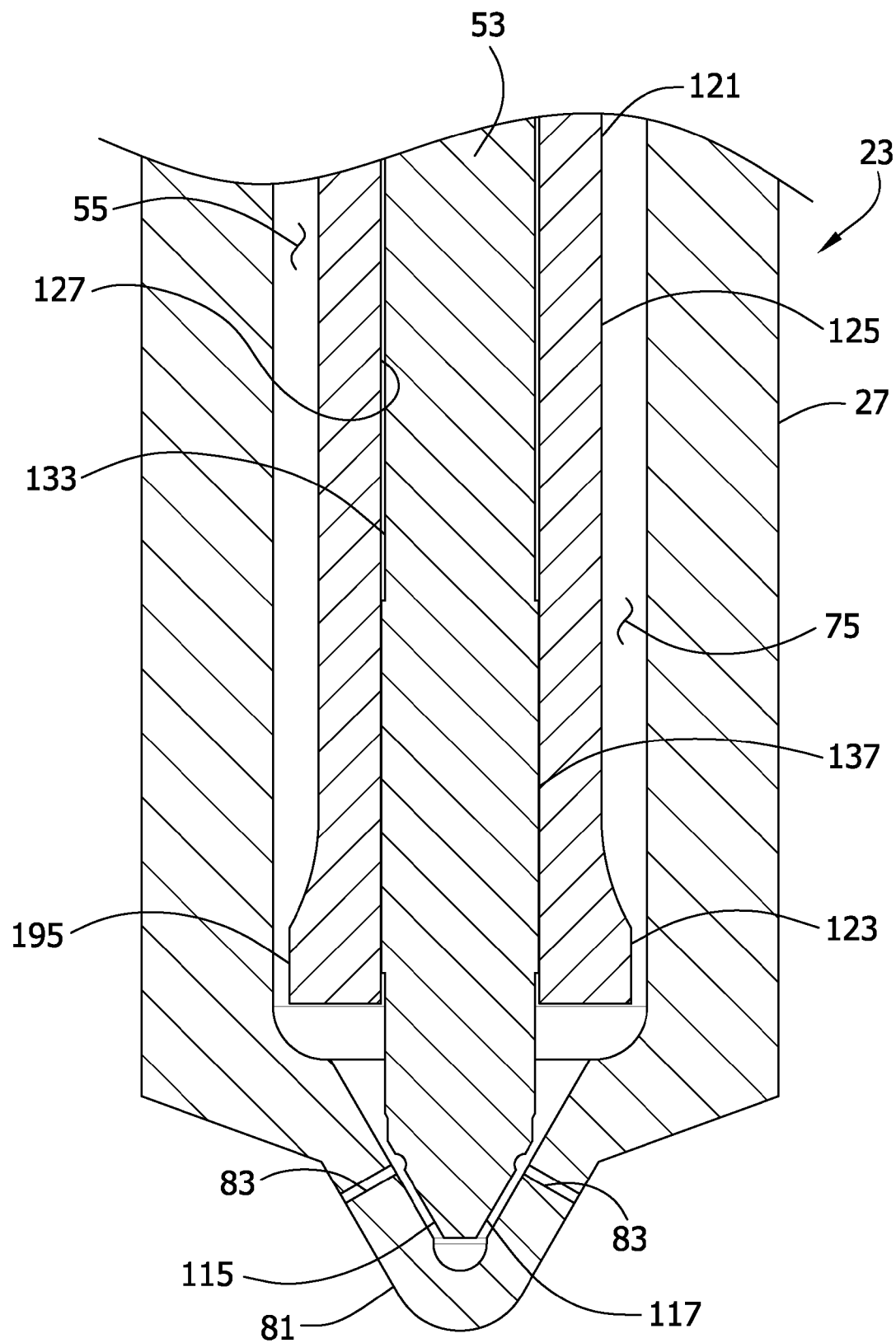
FIG. 7 is an expanded view of a fifth portion of the cross-section of FIG. 1.

With particular reference now to FIGS. 6-8, the illustrated nozzle 27 is generally elongate and is aligned coaxially with the main body 25 of the fuel injector housing 23. In particular, the nozzle 27 has an axial bore 75 aligned coaxially with the axial bore 35 of the main body 25, particularly at the lower end 31 of the main body, so that the main body and nozzle together define the high pressure chamber 55 of the fuel injector housing 23. The cross-sectional dimension of the nozzle bore 75 is stepped outward at the upper end 33 of the nozzle 27 to define a shoulder 77 for seating a mounting member 79 in the fuel injector housing 23. The lower end (also referred to as a tip 81) of the nozzle 27 is generally conical.

Intermediate its tip 81 and upper end 33 the cross-sectional dimension (e.g. the diameter in the illustrated embodiment) of the nozzle bore 75 is generally uniform along the length of the nozzle as illustrated in FIG. 8. One or more exhaust ports 83 (two are visible in the cross-section of FIG. 7 while additional ports are visible in the cross-section of FIG. 10) are formed in the nozzle 27, such as at the tip 81 of the nozzle in the illustrated embodiment, through which high pressure fuel is exhausted from the housing 23 for delivery to the engine. As an example, in one suitable embodiment the nozzle 27 may have eight exhaust ports 83, with each exhaust port having a diameter of about 0.006 inches (0.15 mm). However, it is understood that the number of exhaust ports and the diameter thereof may vary without departing from the scope of this invention. The lower distribution channel 61 and the high pressure chamber 55 together broadly define herein a flow path within the housing 23 along which high pressure fuel flows from the fuel inlet 57 to the exhaust ports 83 of the nozzle 27.

Figure 3:
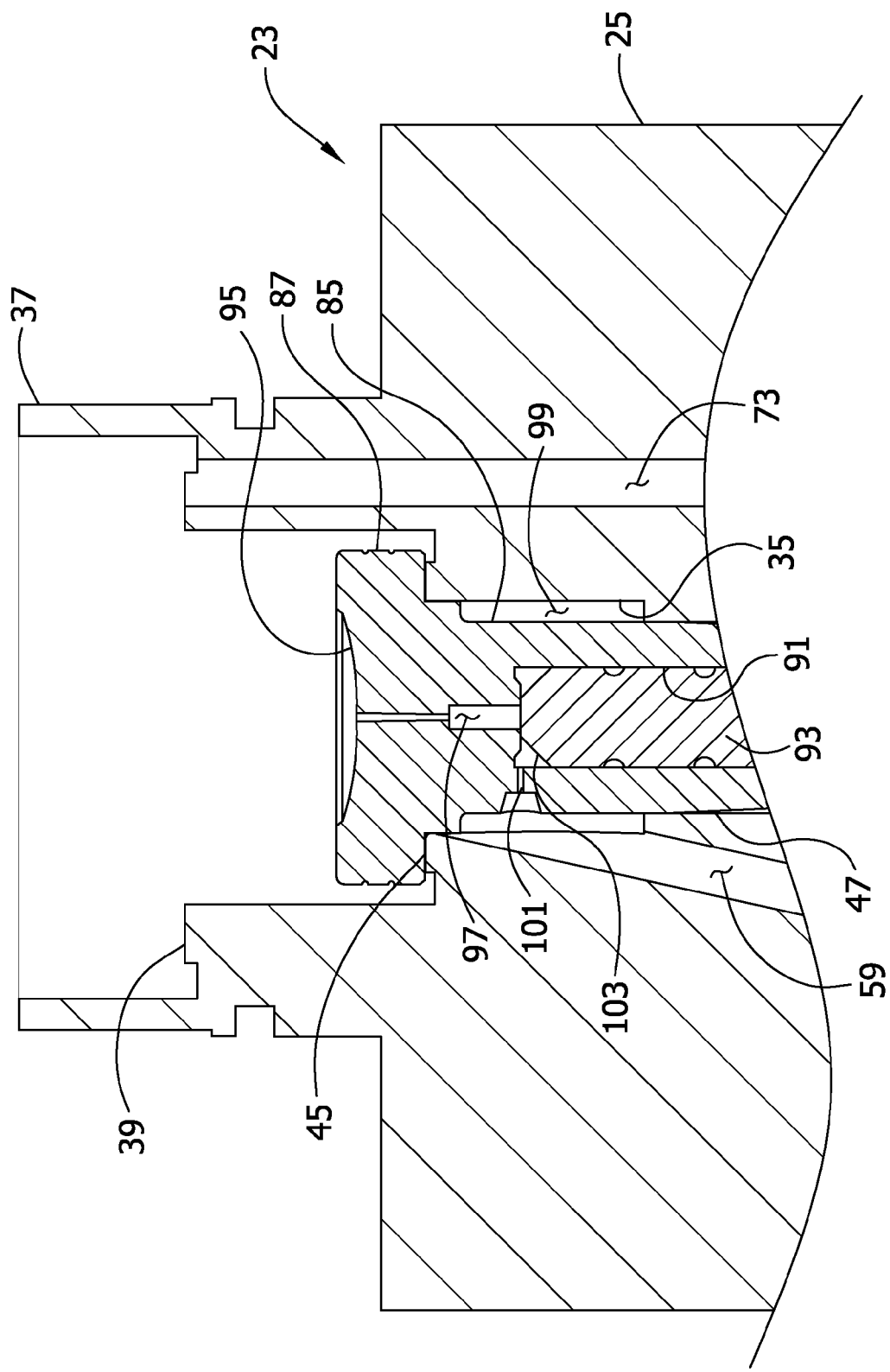
FIG. 3 is an expanded view of a first portion of the cross-section of FIG. 1.

Referring now to FIGS. 1 and 3, the pin holder 47 comprises an elongate, tubular body 85 and a head 87 formed integrally with the upper end of the tubular body and sized in transverse cross-section greater than the tubular body for locating the pin holder on the shoulder 45 of the main body 25 within the central bore 35 thereof. In the illustrated embodiment the pin holder 47 is aligned coaxially with the axial bore 35 of the main body 25, with the tubular body 85 of the pin holder being sized for generally sealing engagement with main body within the axial bore of the main body. The tubular body 85 of the pin holder 47 defines a longitudinally extending internal channel 91 of the pin holder for slidably receiving an elongate pin 93 into the pin holder.

The head 87 of the pin holder 47 has a generally concave, or dish-shaped recess 95 formed centrally in its upper surface, and a bore 97 that extends longitudinally from the center of this recess to the internal channel 91 of the pin holder. As illustrated in FIG. 3, an annular gap 99 is formed between the sidewall of the pin holder 47 and the inner surface of the main body 25 at the upper portion of the bore 35 of the main body. A feed channel 101 extends transversely through the sidewall of the tubular body 85 of the pin holder 47 to the internal channel 91 generally at the upper end of the channel, with the feed channel 101 being open at its transverse outer end to the annular gap 99. The feed channel 101 is in fluid communication with the upper distribution channel 59 in the main body 25 via the annular gap 99 for receiving high pressure fuel into the feed channel, the internal channel of the tubular body 85 above the pin 93, and the bore 97 extending longitudinally within the head 87 of the pin holder 47.

The pin 93 is elongate and suitably extends coaxially within the pin holder channel 91 and axial bore 35 of the main body 25. An upper segment of the pin 93 is slidably received within the internal channel 91 of the pin holder 47 in closely spaced relationship therewith while the remainder of the pin extends longitudinally outward from the pin holder down into the low pressure chamber 49 of the bore 35 of the main body 25. As illustrated in FIG. 3, an upper end 103 of the pin 93 (e.g., at the top of the internal channel 101 of the pin holder 47) is tapered to permit high pressure fuel to be received within the internal channel of the pin holder above the upper end of the pin.

Also disposed within the low pressure chamber 49 of the main body bore 35 are a tubular sleeve 107 (FIG. 4) that surrounds the pin 93 just below the pin holder 47 (e.g., abutting up against the bottom of the pin holder) and defines a spring seat, a hammer 109 abutting against the lower end of the pin in coaxial relationship with the pin and having an upper end that defines an opposing spring seat, and a coil spring 111 retained between the hammer and the spring sleeve with the pin passing longitudinally through the spring.

Figure 2:
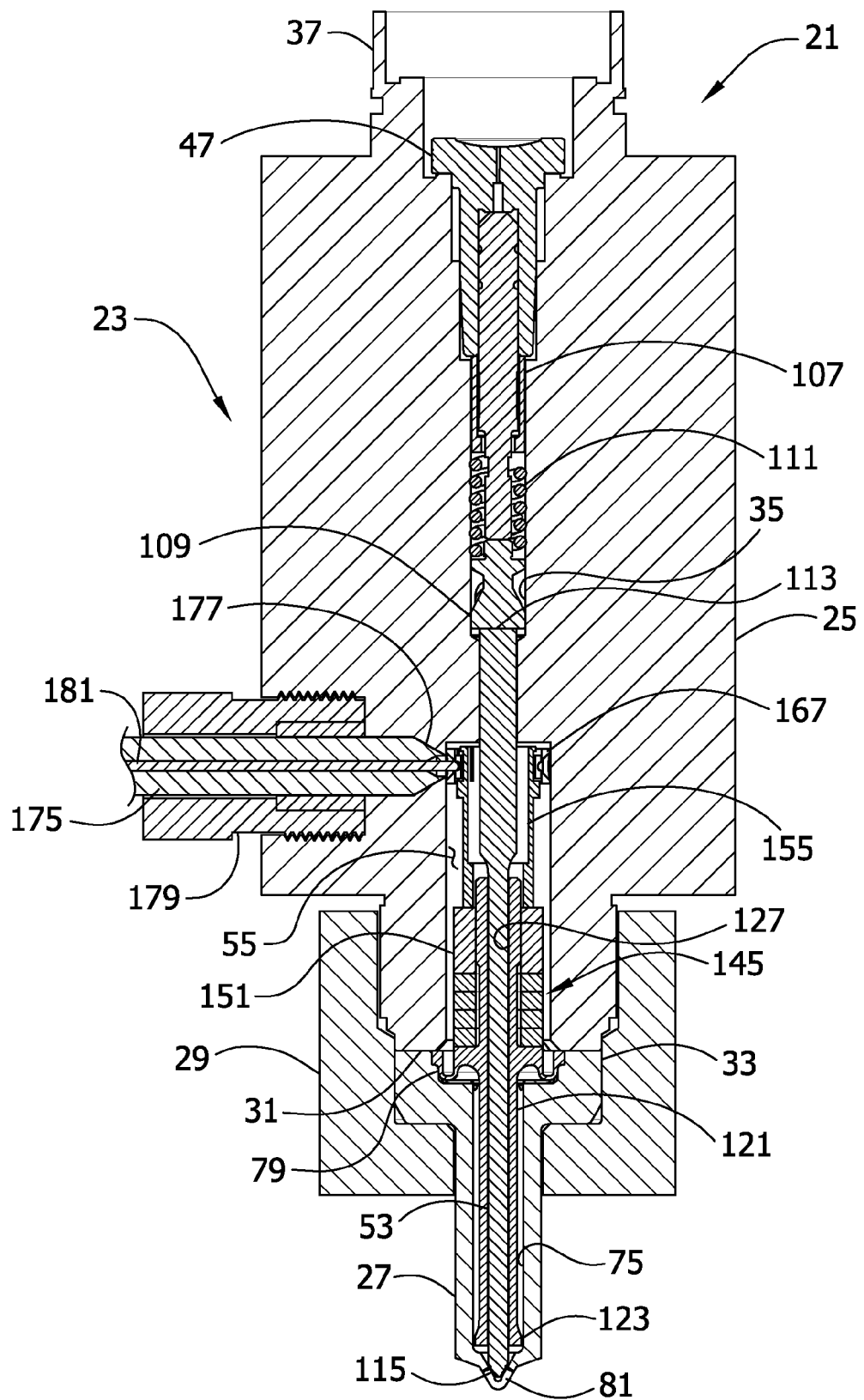
FIG. 2 is a longitudinal cross-section of the fuel injector of FIG. 1 taken at an angular position different from that at which the cross-section of FIG. 1 is taken.

The valve needle 53 (broadly, the valve member) is elongate and extends coaxially within the bore 35 of the main body 25 from an upper end 113 (FIG. 2) of the valve needle in abutment with the bottom of the hammer 109, down through the guide channel segment 51 (FIG. 8) of the main body bore, and further down through the high pressure chamber 55 to a terminal end 115 of the valve needle disposed in close proximity to the tip 81 of the nozzle 27 within the high pressure chamber. As illustrated best in FIGS. 4 and 8, the valve needle 53 is sized in transverse cross-section for closely spaced relationship with the main body 25 in the guide channel segment 51 of the axial bore 35 to maintain proper alignment of the valve needle relative to the nozzle 27.

Referring particularly to FIG. 7, the terminal end 115 of the illustrated valve needle 53 is generally conical in accordance with the conical shape of the tip 81 of the nozzle 27 and defines a closure surface 117 adapted for generally sealing against the inner surface of the nozzle tip in a closed position (not shown) of the valve needle. In particular, in the closed position of the valve needle 53 the closure surface 117 of the valve needle seals against the inner surface of the nozzle tip 81 over the exhaust ports 83 to seal the nozzle (and more broadly the fuel injector housing 23) against fuel being exhausted from the nozzle via the exhaust ports. In an open position of the valve needle (illustrated in FIG. 7), the closure surface 117 of the valve needle 53 is spaced from the inner surface of the nozzle tip 81 to permit fuel in the high pressure chamber 55 to flow between the valve needle 53 and nozzle tip 81 to the exhaust ports 83 for exhaustion from the fuel injector 21.

In general, the spacing between the closure surface 117 of the valve needle terminal end 115 and the opposed surface of nozzle tip 81 in the open position of the valve needle is suitably in the range of about 0.002 inches (0.051 mm) to about 0.025 inches (0.64 mm). However, it is understood that the spacing may be greater or less than the range specified above without departing from the scope of this invention.

It is contemplated that the nozzle 27, and more particularly the tip 81, may be alternatively configured such that the exhaust ports 83 are disposed other than on the nozzle inner surface that seats the closure surface 117 of the valve needle 53 in the closed position of the valve needle. For example, the exhaust ports 83 may be disposed downstream (in the direction in which fuel flows toward the exhaust ports) of the nozzle surface that seats the closure surface 117 of the valve needle 53 and remain within the scope of this invention. One suitable example of such a valve needle, nozzle tip and exhaust port arrangement is described in U.S. Pat. No. 6,543,700, the disclosure of which is incorporated herein by reference to the extent it is consistent herewith.

It will be understood that the pin 93, the hammer 109 and the valve needle 53 are thus conjointly moveable longitudinally on a common axis within the fuel injector housing 23 between the closed position and the open position of the valve needle. The spring 111 disposed between the sleeve 107 and the hammer 109 suitably biases the hammer, and thus the valve needle 53, toward the closed position of the valve needle. It is understood that other suitable valve configurations are possible for controlling the flow of fuel from the injector for delivery to the engine without departing from the scope of this invention. For example, the nozzle 27 (broadly, the housing 23) may have an opening through which the valve needle 53 extends outward of the nozzle and through which fuel exits the nozzle for delivery to the engine. In such an embodiment the terminal end 115 of the valve needle 53 would seal against the nozzle 27 exterior thereof in the closed position of the valve needle. It is also understood that operation of the valve needle 53 may be controlled other than by a solenoid valve and remain within the scope of this invention. It is further understood that the valve needle 53 or other valve arrangement may be omitted altogether from the fuel injector 21 without departing from the scope of this invention.

Figure 9:
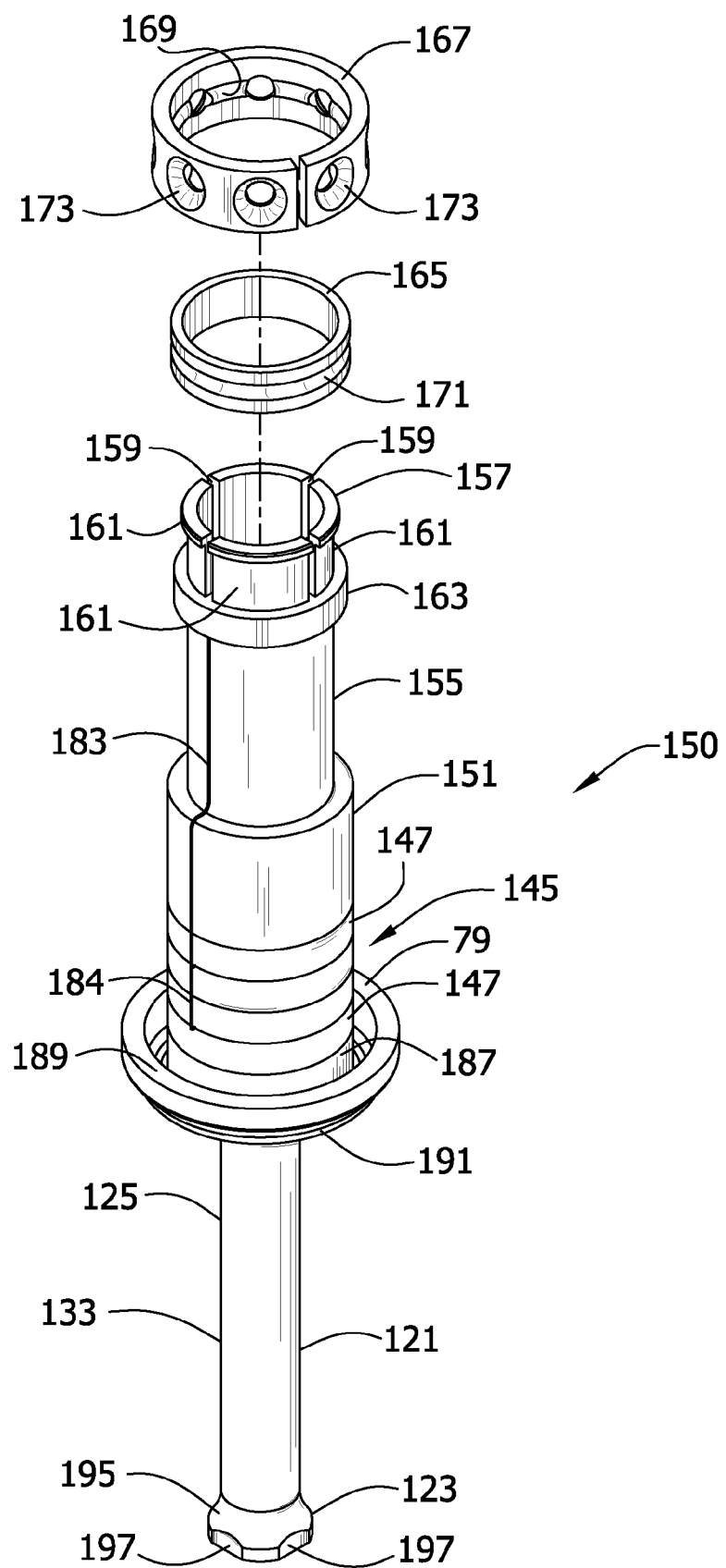
FIG. 9 is a perspective view of a waveguide assembly and other internal components of the fuel injector of FIG. 1.

With particular reference now to FIGS. 8 and 9, an ultrasonic waveguide 121 is formed separate from the valve needle 53 and the fuel injector housing 23 and extends longitudinally within the high pressure chamber 55 of the housing to a terminal end 123 of the waveguide disposed just above the tip 81 of the nozzle 27 to ultrasonically energize fuel in the fuel chamber just prior to the fuel exiting the injector 21 via the exhaust ports 83 formed in the nozzle. The illustrated waveguide 121 is suitably elongate and tubular, having a sidewall 125 defining an internal passage 127 that extends along its length between longitudinally opposite upper and lower ends (the upper end being indicated at 129) of the waveguide. The lower end of the waveguide 121 defines the terminal end 123 of the waveguide. The illustrated waveguide 121 has a generally annular (i.e., circular) cross-section. However, it is understood that the waveguide 121 may be shaped in cross-section other than annular without departing from the scope of this invention. It is also contemplated that the waveguide 121 may be tubular along less than its entire length, and may even be generally solid along its length. In other embodiments, it is contemplated that the valve needle may be generally tubular and the waveguide disposed at least in part within the interior of the valve needle.

In general, the waveguide may be constructed of a metal having suitable acoustical and mechanical properties. Examples of suitable metals for construction of the waveguide include, without limitation, aluminum, monel, titanium, and some alloy steels. It is also contemplated that all or part of the waveguide may be coated with another metal. The ultrasonic waveguide 121 is secured within the fuel injector housing 23, and more suitably in the high pressure chamber 55 as in the illustrated embodiment, by the mounting member 79. The mounting member 79, located longitudinally between the ends 123, 129 of the waveguide 121, generally defines an upper segment 131 of the waveguide that extends longitudinally up (in the illustrated embodiment) from the mounting member 79 to the upper end 129 of the waveguide and a lower segment 133 that extends longitudinally down from the mounting member to the terminal end 123 of the waveguide.

While in the illustrated embodiment the waveguide 121 (i.e., both the upper and lower segments thereof) is disposed entirely within the high pressure chamber 55 of the housing, it is contemplated that only a portion of the waveguide may be disposed within the high pressure chamber without departing from the scope of this invention. For example, only the lower segment 133 of the waveguide 121, including the terminal end 123 thereof, may be disposed within the high pressure chamber 55 while the upper segment 131 of the waveguide is disposed exterior of the high pressure chamber, and may or may not be subjected to high pressure fuel within the injector housing 23.

The inner cross-sectional dimension (e.g., inner diameter in the illustrated embodiment) of the waveguide 121 (e.g., the cross-sectional dimension of the interior passage 127 thereof) is generally uniform along the length of the waveguide and is suitably sized to accommodate the valve needle 53, which extends coaxially within the interior passage of the waveguide along the full length of the waveguide (and above the waveguide into abutment with the hammer 109 in the illustrated embodiment). It is understood, however, that the valve needle 53 may extend only along a portion of the interior passage 127 of the waveguide 121 without departing from the scope of this invention. It is also understood that the inner cross-sectional dimension of the waveguide 121 may be other than uniform along the length of the waveguide. In the illustrated embodiment, the terminal end 115 of the valve needle 53, and more suitably the closure surface 117 of the valve needle, is disposed longitudinally outward of the terminal end 123 of the waveguide 121 in both the open and closed positions of the valve needle. It is understood, however, that the closure surface 117 of the terminal end 115 of the valve needle 53 need only extend outward of the terminal end 123 of the waveguide 121 in the closed position of the valve needle and may be disposed fully or partially within the interior passage 127 of the waveguide in the open position of the valve needle.

As illustrated best in FIG. 7, the cross-sectional dimension (e.g., the diameter in the illustrated embodiment) of the portion of the valve needle 53 extending within the interior passage 127 of the waveguide 121 is sized slightly smaller than the cross-sectional dimension of the interior passage of the waveguide to define in part the flow path for high pressure fuel within the housing, and more suitably define a part of the flow path that extends between the inner surface of the waveguide sidewall 125 and the valve needle along the length of the valve needle. For example, in one embodiment the valve needle 53 is transversely spaced (e.g., radially spaced in the illustrated embodiment) from the inner surface of the waveguide sidewall 125 within the interior passage 127 of the waveguide in the range of about 0.0005 inches (0.013 mm) to about 0.0025 inches (0.064 mm).

Along a pair of longitudinally spaced segments (e.g., one segment 137 (FIG. 7) being adjacent the terminal end 123 of the waveguide 121 and the other segment 139 (FIG. 6a) being adjacent and just above the mounting member 79) of the valve needle 53 within the passage 127, the cross-sectional dimension of the valve needle 53 is increased so that the valve needle is in a more closely spaced or even sliding contact relationship with the waveguide within the passage to facilitate proper alignment therein and to inhibit transverse movement of the valve needle within the passage. The outer surface of the valve needle 53 at these segments has one or more flats (not shown) formed therein to in part define the portion of the flow path that extends within the interior passage 127 of the waveguide 121. Alternatively, the valve needle 53 outer surface may be longitudinally fluted at these segments to permit fuel to flow within the interior passage 127 of the waveguide 121 past such segments.

With particular reference to FIG. 7, the outer surface of the waveguide sidewall 125 is spaced transversely from the main body 25 and nozzle 27 to further define the flow path along which high pressure fuel flows from the fuel inlet 57 to the exhaust ports 83, and more suitably forms a portion of the flow path exterior, or outward of the waveguide 121. In general, the outer cross-sectional dimension (e.g., outer diameter in the illustrated embodiment) of the waveguide sidewall 125 is uniform along a length thereof intermediate an enlarged portion 195 of the waveguide disposed longitudinally at and/or adjacent the terminal end 123 of the waveguide 121, and another enlarged portion 153 disposed longitudinally adjacent the upper end 129 of the waveguide. As an example, the transverse (e.g., radial in the illustrated embodiment) spacing between the waveguide sidewall 125 and the nozzle 27 upstream (e.g., relative to the direction in which fuel flows from the upper end 33 of the nozzle to the exhaust ports 83) of the terminal end 123 of the waveguide is suitably in the range of about 0.001 inches (0.025 mm) to about 0.021 inches (0.533 mm). However, the spacing may be less than or greater than that without departing from the scope of this invention.

The outer cross-sectional dimension of the portion 195 of the lower segment 133 of the waveguide 121 suitably increases, and more suitably tapers or flares transversely outward adjacent to or more suitably at the terminal end 123 of the waveguide. For example, the cross-sectional dimension of this enlarged portion 195 of the lower segment 133 of the waveguide 121 is sized for closely spaced or even sliding contact relationship with the nozzle 27 within the central bore 75 thereof to maintain proper axial alignment of the waveguide (and hence the valve needle 53) within the high pressure chamber 55.

As a result, the portion of the flow path between the waveguide 121 and the nozzle 27 is generally narrower adjacent to or at the terminal end 123 of the waveguide relative to the flow path immediately upstream of the terminal end of the waveguide to generally restrict the flow of fuel past the terminal end of the waveguide to the exhaust ports 83. The enlarged portion 195 of the lower segment 133 of the waveguide 121 also provides increased ultrasonically excited surface area to which the fuel flowing past the terminal end 123 of the waveguide is exposed. One or more flats 197 (FIG. 9) are formed in the outer surface of the enlarged portion 195 of the lower segment 133 to facilitate the flow of fuel along the flow path past the terminal end 123 of the waveguide 121 for flow to the exhaust ports 83 of the nozzle 27. It is understood that the enlarged portion 195 of the waveguide sidewall 115 may be stepped outward instead of tapered or flared. It is also contemplated the upper and lower surfaces of the enlarged portion 195 may be contoured instead of straight and remain within the scope of this invention.

In one example, the enlarged portion 195 of the waveguide lower segment 133, e.g., at and/or adjacent the terminal end 123 of the waveguide, has a maximum outer cross-sectional dimension (e.g., outer diameter in the illustrated embodiment) of about 0.2105 inches (5.35 mm), whereas the maximum outer cross-sectional dimension of the waveguide immediately upstream of this enlarged portion may be in the range of about 0.16 inches (4.06 mm) to slightly less than about 0.2105 inches (5.35 mm).

The transverse spacing between the terminal end 123 of the waveguide 121 and the nozzle 27 defines an open area through which fuel flows along the flow path past the terminal end of the waveguide. The one or more exhaust ports 83 define an open area through which fuel exits the housing 23. For example, where one exhaust port is provided the open area through which fuel exits the housing 23 is defined as the cross-sectional area of the exhaust port (e.g., where fuel enters into the exhaust port) and where multiple exhaust ports 83 are present the open area through which fuel exits the housing is defined as the sum of the cross-sectional area of each exhaust port. In one embodiment, a ratio of the open area at the terminal end 123 of the waveguide 121 and the nozzle 27 to the open area through which fuel exits the housing 23 (e.g. at exhaust ports 83) is suitably in the range of about 4:1 to about 20:1.

It is understood that in other suitable embodiments the lower segment 133 of the waveguide 121 may have a generally uniform outer cross-sectional dimension along its entire length (e.g. such that no enlarged portion 195 is formed), or may decrease in outer cross-sectional dimension (e.g., substantially narrow towards its terminal end 123) without departing from the scope of the invention.

Referring again to FIGS. 8 and 9, an excitation device adapted to energize the waveguide 121 to mechanically vibrate ultrasonically is suitably disposed entirely within the high pressure chamber 55 along with the waveguide and is generally indicated at 145. In one embodiment, the excitation device 145 is suitably responsive to high frequency (e.g., ultrasonic frequency) electrical current to vibrate the waveguide ultrasonically. As an example, the excitation device 145 may suitably receive high frequency electrical current from a suitable generating system (not shown) that is operable to deliver high frequency alternating current to the excitation device. The term "ultrasonic' as used herein is taken to mean having a frequency in the range of about 15 kHz to about 100 kHz. As an example, in one embodiment the generating system may suitably deliver alternating current to the excitation device at an ultrasonic frequency in the range of about 15 kHz to about 100 kHz, more suitably in the range of about 15 kHz to about 60 kHz, and even more suitably in the range of about 20 kHz to about 40 kHz. Such generating systems are well known to those skilled in the art and need not be further described herein.

In the illustrated embodiment the excitation device 145 comprises a piezoelectric device, and more suitably a plurality of stacked piezoelectric rings 147 (e.g., at least two and in the illustrated embodiment four) surrounding the upper segment 131 of the waveguide 121 and seated on a shoulder 149 formed by the mounting member 79. An annular collar 151 surrounds the upper segment 131 of the waveguide 121 above the piezoelectric rings 147 and bears down against the uppermost ring. Suitably, the collar 151 is constructed of a high density material. For example, one suitable material from which the collar 151 may be constructed is tungsten. It is understood, however, that the collar 151 may be constructed of other suitable materials and remain within the scope of this invention. The enlarged portion 153 adjacent the upper end 129 of the waveguide 121 has an increased outer cross-sectional dimension (e.g., an increased outer diameter in the illustrated embodiment) and is threaded along this segment. The collar 151 is internally threaded to threadably fasten the collar on the waveguide 121. The collar 151 is suitably tightened down against the stack of piezoelectric rings 147 to compress the rings between the collar and the shoulder 149 of the mounting member 79.

The waveguide 121 and excitation device 145 of the illustrated embodiment together broadly define a waveguide assembly, indicated generally at 150, for ultrasonically energizing the fuel in the high pressure chamber 55. Accordingly, the entire waveguide assembly 150 is disposed entirely within the high pressure fuel chamber 55 of the fuel injector 21 and is thus generally uniformly exposed to the high pressure environment within the fuel injector. As an example, the illustrated waveguide assembly is particularly constructed to act as both an ultrasonic horn and a transducer to ultrasonically vibrate the ultrasonic horn. In particular, the lower segment 133 of the waveguide 121 as illustrated in FIG. 8 generally acts in the manner of an ultrasonic horn while the upper segment 131 of the waveguide, and more suitably the portion of the upper segment that extends generally from the mounting member 79 to the location at which the collar 151 fastens to the upper segment of the waveguide together with the excitation device (e.g., the piezoelectric rings) acts in the manner of a transducer.

Upon delivering electrical current (e.g., alternating current delivered at an ultrasonic frequency) to the piezoelectric rings 147 of the illustrated embodiment the piezoelectric rings expand and contract (particularly in the longitudinal direction of the fuel injector 21) at the ultrasonic frequency at which current is delivered to the rings. Because the rings 147 are compressed between the collar 151 (which is fastened to the upper segment 131 of the waveguide 21) and the mounting member 79, expansion and contraction of the rings causes the upper segment of the waveguide to elongate and contract ultrasonically (e.g., generally at the frequency that the piezoelectric rings expand and contract), such as in the manner of a transducer. Elongation and contraction of the upper segment 131 of the waveguide 121 in this manner excites the resonant frequency of the waveguide, and in particular along the lower segment 133 of the waveguide, resulting in ultrasonic vibration of the waveguide along the lower segment, e.g., in the manner of an ultrasonic horn.

As an example, in one embodiment the displacement of the lower segment 133 of the waveguide 121 resulting from ultrasonic excitation thereof may be up to about six times the displacement of the piezoelectric rings and upper segment of the waveguide. It is understood, though, that the displacement of the lower segment 133 may be amplified more than six times, or it may not be amplified at all, and remain within the scope of this invention.

It is contemplated that a portion of the waveguide 121 (e.g., a portion of the upper segment 131 of the waveguide) may alternatively be constructed of a magnetostrictive material that is responsive to magnetic fields changing at ultrasonic frequencies. In such an embodiment (not shown) the excitation device may comprise a magnetic field generator disposed in whole or in part within the housing 23 and operable in response to receiving electrical current to apply a magnetic field to the magnetostrictive material wherein the magnetic field changes at ultrasonic frequencies (e.g., from on to off, from one magnitude to another, and/or a change in direction).

For example a suitable generator may comprise an electrical coil connected to the generating system which delivers current to the coil at ultrasonic frequencies. The magnetostrictive portion of the waveguide and the magnetic field generator of such an embodiment thus together act as a transducer while the lower segment 133 of the waveguide 121 again acts as an ultrasonic horn. One example of a suitable magnetostrictive material and magnetic field generator is disclosed in U.S. Pat. No. 6,543,700, the disclosure of which is incorporated herein by reference to the extent it is consistent herewith.

While the entire waveguide assembly 150 is illustrated as being disposed within the high pressure chamber 55 of the fuel injector housing 23, it is understood that one or more components of the waveguide assembly may be wholly or partially disposed exterior of the high pressure chamber, and may even be disposed exterior of the housing, without departing from the scope of this invention. For example, where a magnetostrictive material is used, the magnetic field generator (broadly, the excitation device) may be disposed in the main body 25 or other component of the fuel injector housing 23 and be only partially exposed to or completely sealed off from the high pressure chamber 55. In another embodiment, the upper segment 131 of the waveguide 121 and the piezoelectric rings 147 (and collar 151) may together be located exterior of the high pressure chamber 55 without departing from the scope of this invention, as long as the terminal end 123 of the waveguide is disposed within the high pressure chamber.

By placing the piezoelectric rings 147 and collar 151 about the upper segment 131 of the waveguide 121, the entire waveguide assembly 150 need be no longer than the waveguide itself (e.g., as opposed to the length of an assembly in which a transducer and ultrasonic horn are arranged in a conventional end-to-end, or "stacked" arrangement). As one example, the overall waveguide assembly 150 may suitably have a length equal to about one-half of the resonating wavelength (otherwise commonly referred to as one-half wavelength) of the waveguide. In particular, the waveguide assembly 150 is suitably configured to resonate at an ultrasonic frequency in the range of about 15 kHz to about 100 kHz, more suitably in the range of about 15 kHz to about 60 kHz, and even more suitably in the range of about 20 kHz to about 40 kHz. The one-half wavelength waveguide assembly 150 operating at such frequencies has a respective overall length (corresponding to a one-half wavelength) in the range of about 133 mm to about 20 mm, more suitably in the range of about 133 mm to about 37.5 mm and even more suitably in the range of about 100 mm to about 50 mm. As a more particular example, the waveguide assembly 150 illustrated in FIGS. 8 and 9 is configured for operation at a frequency of about 40 kHz and has an overall length of about 50 mm. It is understood, however, that the housing 23 may be sufficiently sized to permit a waveguide assembly having a full wavelength to be disposed therein. It is also understood that in such an arrangement the waveguide assembly may comprise an ultrasonic horn and transducer in a stacked configuration.

An electrically non-conductive sleeve 155 (which is cylindrical in the illustrated embodiment but may be shaped otherwise) is seated on the upper end of the collar 151 and extends up from the collar to the upper end of the high pressure chamber 55. The sleeve 155 is also suitably constructed of a generally flexible material. As an example, one suitable material from which the sleeve 155 may be constructed is an amorphous thermoplastic polyetherimide material available from General Electric Company, U.S.A., under the tradename ULTEM. However, other suitable electrically non-conductive materials, such as ceramic materials, may be used to construct the sleeve 155 and remain within the scope of this invention. The upper end of the sleeve 155 has an integrally formed annular flange 157 extending radially outward therefrom, and a set of four longitudinally extending slots 159 defining four generally flexible tabs 161 at the upper end of the sleeve. A second annular flange 163 is formed integrally with the sleeve 155 and extends radially outward from the sleeve just below the longitudinally extending slots 159, i.e., in longitudinally spaced relationship with the annular flange 157 disposed at the upper end of the sleeve.

A contact ring 165 constructed of an electrically conductive material circumscribes the sleeve 155 intermediate the longitudinally spaced annular flanges 157, 163 of the sleeve. In one embodiment, the contact ring 165 is suitably constructed of brass. It is understood, however, that the contact ring 165 may be constructed of other suitable electrically conductive materials without departing from the scope of this invention. It also understood that a contact device other than a ring, such as a single point contact device, flexible and/or spring-loaded tab or other suitable electrically conductive device, may be used without departing from the scope of the invention. In the illustrated embodiment, the inner cross-sectional dimension (e.g., the diameter) of the contact ring 165 is sized slightly smaller than the outer cross-sectional dimension of the longitudinal segment of the sleeve 155 extending between the annular flanges 157, 163.

The contact ring 165 is inserted onto the sleeve 155 by urging the contact ring telescopically down over the upper end of the sleeve. The force of the ring 165 against the annular flange 157 at the upper end of the sleeve 155 urges the tabs 161 to flex (e.g. bend) radially inward to allow the ring to slide down past the annular flange formed at the upper end of the sleeve and to seat the ring on the second annular flange 163. The tabs 161 resiliently move back out toward their initial position, providing frictional engagement between the contact ring 165 and the sleeve 155 and retaining the contact ring between the annular flanges 157, 163 of the sleeve.

A guide ring 167 constructed of an electrically non-conductive material circumscribes and electrically insulates the contact ring 165. As an example, the guide ring 167 may (but need not necessarily) be constructed of the same material as the sleeve 163. In one embodiment, the guide ring 167 is suitably retained on the sleeve, and more suitably on the contact ring 165, by a clamping, or frictional fit of the guide ring on the contact ring. For example, the guide ring 167 may be a discontinuous ring broken along a slot as illustrated in FIG. 9. The guide ring 167 is thus circumferentially expandable at the slot to fit the guide ring over the contact ring 165 and upon subsequent release closes resiliently and securely around the contact ring.

In one particularly suitable embodiment, an annular locating nub 169 extends radially inward from the guide ring 167 and is receivable in an annular groove 171 formed in the contact ring 165 to properly locate the guide ring on the contact ring. It is understood, however, that the contact ring 165 and guide ring 167 may be mounted on the sleeve 155 other than as illustrated in FIGS. 8 and 9 without departing from the scope of this invention. At least one, and more suitably a plurality of tapered or frusto-conically shaped openings 173 are formed radially through the guide ring 167 to permit access to the contact ring 165 for delivering electrical current to the contact ring.

Figure 5:
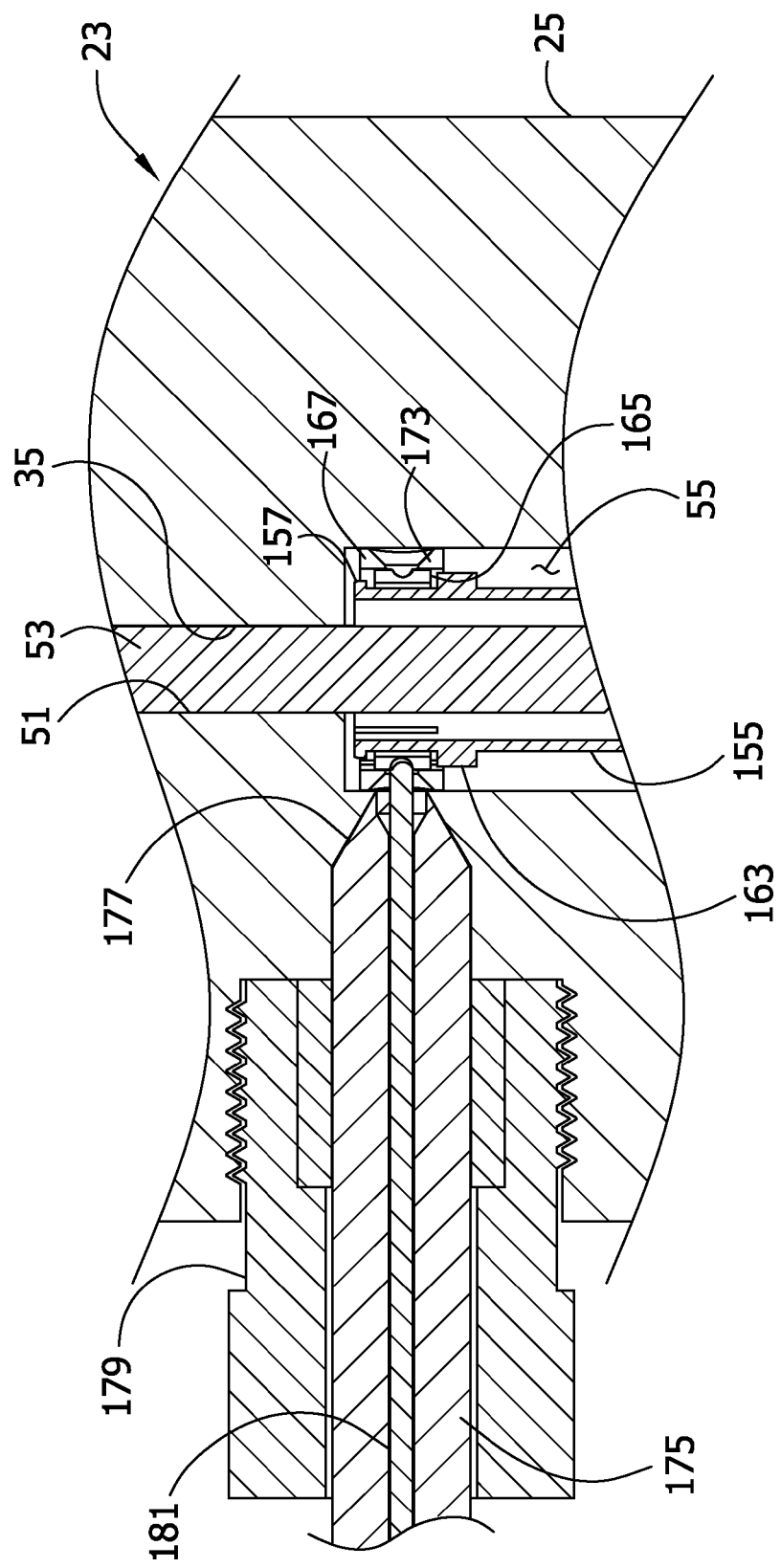
FIG. 5 is an expanded view of a third portion of the cross-section of FIG. 2.

As seen best in FIG. 5, an insulating sleeve 175 constructed of a suitable electrically non-conductive material extends through an opening in the side of the main body 25 and has a generally conically shaped terminal end 177 configured to seat within one of the openings 173 of the guide ring 167. The insulating sleeve 175 is held in place by a suitable fitting 179 that threadably fastens to the main body 25 within the opening 173 and has a central opening through which the insulating sleeve extends. Suitable electrical wiring 181 extends through the insulating sleeve 175 into electrical contact with the contact ring 165 at one end of the wire and is in electrical communication at its opposite end (not shown) with a source (not shown) of electrical current.

Additional electrical wiring 183 extends from the contact ring 165 down along the outside of the sleeve 155 within the high pressure chamber 55 and into electrical communication with an electrode (not shown) disposed between the uppermost piezoelectric ring 147 and the next lower piezoelectric ring. A separate wire 184 electrically connects the electrode to another electrode (not shown) disposed between the lowermost piezoelectric ring 147 and the ring just above it. The mounting member 79 and/or the waveguide 121 provide the ground for the current delivered to the piezoelectric rings 147. In particular, a ground wire 185 is connected to the mounting member 79 and extends up to between the middle two piezoelectric rings 147 into contact with an electrode (not shown) disposed therebetween. Optionally, a second ground wire (not shown) may extend from between the middle two piezoelectric rings 147 into contact with another electrode (not shown) between the uppermost piezoelectric ring and the collar 151.

With particular reference now to FIGS. 6, 6a, 8 and 9, the mounting member 79 is suitably connected to the waveguide 121 intermediate the ends 123, 129 of the waveguide. More suitably, the mounting member 79 is connected to the waveguide 121 at a nodal region of the waveguide. As used herein, the "nodal region" of the waveguide 121 refers to a longitudinal region or segment of the waveguide along which little (or no) longitudinal displacement occurs during ultrasonic vibration of the waveguide and transverse (e.g., radial in the illustrated embodiment) displacement is generally maximized. Transverse displacement of the waveguide 121 suitably comprises transverse expansion of the waveguide but may also include transverse movement (e.g., bending) of the waveguide.

In the illustrated embodiment, the configuration of the waveguide 121 is such that a nodal plane (i.e., a plane transverse to the waveguide at which no longitudinal displacement occurs while transverse displacement is generally maximized) is not present. Rather, the nodal region of the illustrated waveguide 121 is generally dome-shaped such that at any given longitudinal location within the nodal region some longitudinal displacement may still be present while the primary displacement of the waveguide is transverse displacement.

It is understood, however, that the waveguide 121 may be suitably configured to have a nodal plane (or nodal point as it is sometimes referred to) and that the nodal plane of such a waveguide is considered to be within the meaning of nodal region as defined herein. It is also contemplated that the mounting member 79 may be disposed longitudinally above or below the nodal region of the waveguide 121 without departing from the scope of the invention.

The mounting member 79 is suitably configured and arranged in the fuel injector 21 to vibrationally isolate the waveguide 121 from the fuel injector housing 23. That is, the mounting member 25 inhibits the transfer of longitudinal and transverse (e.g., radial) mechanical vibration of the waveguide 121 to the fuel injector housing 23 while maintaining the desired transverse position of the waveguide within the high pressure chamber 55 and allowing longitudinal displacement of the waveguide within the fuel injector housing. As one example, the mounting member 79 of the illustrated embodiment generally comprises an annular inner segment 187 extending transversely (e.g., radially in the illustrated embodiment) outward from the waveguide 121, an annular outer segment 189 extending transverse to the waveguide in transversely spaced relationship with the inner segment, and an annular interconnecting web 191 extending transversely between and interconnecting the inner and outer segments. While the inner and outer segments 187, 189 and interconnecting web 191 extend continuously about the circumference of the waveguide 121, it is understood that one or more of these elements may be discontinuous about the waveguide such as in the manner of wheel spokes, without departing from the scope of this invention.

Figure 6A:
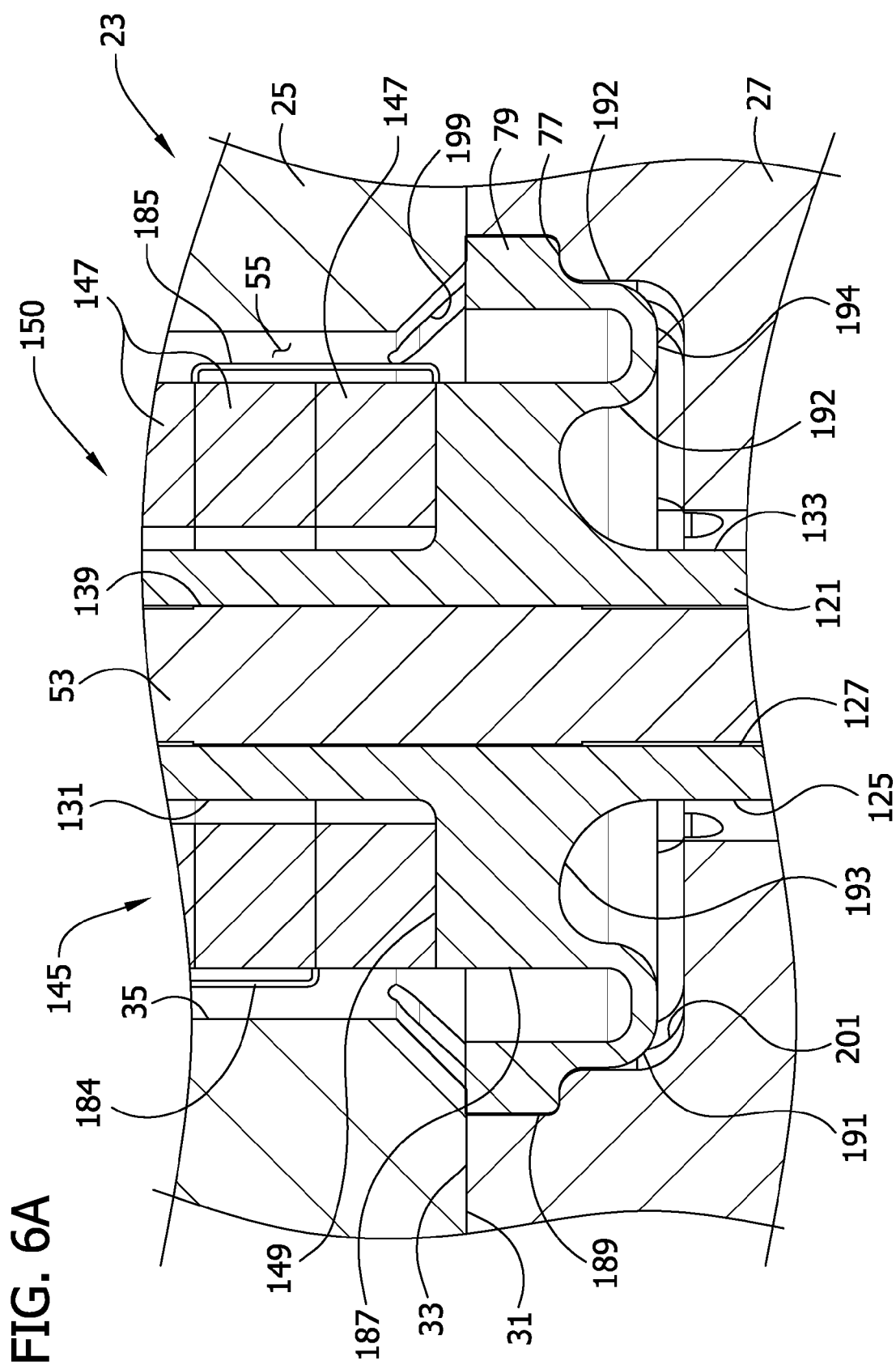
FIG. 6a is an expanded view of a central portion of the cross-section of FIG. 1.

In the embodiment illustrated in FIG. 6a, the inner segment 187 of the mounting member 79 has a generally flat upper surface that defines the shoulder 149 on which the excitation device 145, e.g., the piezoelectric rings 147, is seated. A lower surface 193 of the inner segment 187 is suitably contoured as it extends from adjacent the waveguide 121 to its connection with the interconnecting web 191, and more suitably has a blended radius contour. In particular, the contour of the lower surface 193 at the juncture of the web 191 and the inner segment 187 of the mounting member 79 is suitably a smaller radius (e.g., a sharper, less tapered or more corner-like) contour to facilitate distortion of the web during vibration of the waveguide 121. The contour of the lower surface 193 at the juncture of the inner segment 187 of the mounting member 79 and the waveguide 121 is suitably a relatively larger radius (e.g., a more tapered or smooth) contour to reduce stress in the inner segment of the mounting member upon distortion of the interconnecting web 191 during vibration of the waveguide.

The outer segment 189 of the mounting member 79 is configured to seat down against a shoulder formed by the nozzle 27 generally adjacent the upper end 33 of the nozzle. As seen best in FIG. 6, the internal cross-sectional dimension (e.g., internal diameter) of the nozzle 27 is stepped inward adjacent the upper end 33 of the nozzle, e.g., longitudinally below the mounting member 79, so that that nozzle is longitudinally spaced from the contoured lower surface 193 of the inner segment 187 and interconnecting web 191 of the mounting member to allow for displacement of the mounting member during ultrasonic vibration of the waveguide 121. The mounting member 79 is suitably sized in transverse cross-section so that at least an outer edge margin of the outer segment 189 is disposed longitudinally between the shoulder of the nozzle 27 and the lower end 31 of the main body 25 of the fuel injector housing 23 (i.e., the surface of the main body that seats against the upper end 33 of the nozzle). The retaining member 29 of the fuel injector 21 urges the nozzle 27 and the main body 25 together to secure the edge margin of the mounting member outer segment 189 therebetween.

The interconnecting web 191 is constructed to be relatively thinner than the inner and outer segments 187, 189 of the mounting member 79 to facilitate flexing and/or bending of the web in response to ultrasonic vibration of the waveguide 121. As an example, in one embodiment the thickness of the interconnecting web 191 of the mounting member 79 may be in the range of about 0.2 mm to about 1 mm, and more suitably about 0.4 mm. The interconnecting web 191 of the mounting member 79 suitably comprises at least one axial component 192 and at least one transverse (e.g., radial in the illustrated embodiment) component 194. In the illustrated embodiment, the interconnecting web 191 has a pair of transversely spaced axial components 192 connected by the transverse component 194 such that the web is generally U-shaped in cross-section.

It is understood, however, that other configurations that have at least one axial component 192 and at least one transverse component 194 are suitable, such as L-shaped, H-shaped, I-shaped, inverted U-shaped, inverted L-shaped, and the like, without departing from the scope of this invention. Additional examples of suitable interconnecting web 191 configurations are illustrated and described in U.S. Pat. No. 6,676,003, the disclosure of which is incorporated herein by reference to the extent it is consistent herewith.

The axial components 192 of the web 191 depend from the respective inner and outer segments 187, 189 of the mounting member and are generally cantilevered to the transverse component 194. Accordingly, the axial component 192 is capable of dynamically bending and/or flexing relative to the outer segment 189 of the mounting member in response to transverse vibratory displacement of the inner segment 187 of the mounting member to thereby isolate the housing 23 from transverse displacement of the waveguide. The transverse component 194 of the web 191 is cantilevered to the axial components 192 such that the transverse component is capable of dynamically bending and flexing relative to the axial components (and hence relative to the outer segment 189 of the mounting member) in response to axial vibratory displacement of the inner segment 187 to thereby isolate the housing 23 from axial displacement of the waveguide.

In the illustrated embodiment, the waveguide 121 expands radially as well as displaces slightly axially at the nodal region (e.g., where the mounting member 79 is connected to the waveguide) upon ultrasonic excitation of the waveguide. In response, the U-shaped interconnecting member 191 (e.g., the axial and transverse components 192, 194 thereof) generally bends and flexes, and more particularly rolls relative to the fixed outer segment 189 of the mounting member 79, e.g., similar to the manner in which a toilet plunger head rolls upon axial displacement of the plunger handle. Accordingly, the interconnecting web 79 isolates the fuel injector housing 23 from ultrasonic vibration of the waveguide 121, and in the illustrated embodiment it more particularly isolates the outer segment 189 of the mounting member from vibratory displacement of the inner segment 187 thereof. Such a mounting member 79 configuration also provides sufficient bandwidth to compensate for nodal region shifts that can occur during ordinary operation. In particular, the mounting member 79 can compensate for changes in the real time location of the nodal region that arise during the actual transfer of ultrasonic energy through the waveguide 121. Such changes or shifts can occur, for example, due to changes in temperature and/or other environmental conditions within the high pressure chamber 55.

While in the illustrated embodiment the inner and outer segments 187, 189 of the mounting member 79 are disposed generally at the same longitudinal location relative to the waveguide, it is understood that the inner and outer segments may be longitudinally offset from each other without departing from the scope of this invention. It is also contemplated that the interconnecting web 191 may comprise only one or more axial components 192 (e.g., the transverse component 194 may be omitted) and remain within the scope of this invention. For example where the waveguide 121 has a nodal plane and the mounting member 79 is located on the nodal plane, the mounting member need only be configured to isolate the transverse displacement of the waveguide. In an alternative embodiment (not shown), it is contemplated that the mounting member may be disposed at or adjacent an anti-nodal region of the waveguide, such as at one of the opposite ends 123, 129 of the waveguide. In such an embodiment, the interconnecting web 191 may comprise only one or more transverse components 194 to isolate axial displacement of the waveguide (i.e., little or no transverse displacement occurs at the anti-nodal region).

In one particularly suitable embodiment the mounting member 79 is of single piece construction. Even more suitably the mounting member 79 may be formed integrally with the waveguide 121 as illustrated in FIG. 6. However, it is understood that the mounting member 79 may be constructed separate from the waveguide 121 and remain within the scope of this invention. It is also understood that one or more components of the mounting member 79 may be separately constructed and suitably connected or otherwise assembled together.

In one suitable embodiment the mounting member 79 is further constructed to be generally rigid (e.g., resistant to static displacement under load) so as to hold the waveguide 121 (and hence the valve needle 53) in proper alignment within the high pressure chamber 55. For example, the rigid mounting member in one embodiment may be constructed of a non-elastomeric material, more suitably metal, and even more suitably the same metal from which the waveguide is constructed. The term rigid is not, however, intended to mean that the mounting member is incapable of dynamic flexing and/or bending in response to ultrasonic vibration of the waveguide. In other embodiments, the rigid mounting member may be constructed of an elastomeric material that is sufficiently resistant to static displacement under load but is otherwise capable of dynamic flexing and/or bending in response to ultrasonic vibration of the waveguide. While the mounting member 79 illustrated in FIG. 6 is constructed of a metal, and more suitably constructed of the same material as the waveguide 121, it is contemplated that the mounting member may be constructed of other suitable generally rigid materials without departing from the scope of this invention.

With reference back to FIGS. 6 and 8, the flow path along which fuel flows within the high pressure chamber 55 of the fuel injector housing 23 is defined in part by the transverse spacing between the inner surface of the nozzle 27 and the outer surface of the lower segment 133 of the waveguide 121 (e.g., below the mounting member 79), and between the inner surface of the main body 25 and the outer surfaces of the excitation device 145, the collar 151 and the sleeve 155 (e.g. above the mounting member). The fuel flow path is in fluid communication with the fuel inlet 57 of the main body 25 of the injector housing 23 generally at the sleeve 155 such that high pressure fuel entering the flow path from the fuel inlet flows down (in the illustrated embodiment) along the flow path toward the nozzle tip 81 for exhaustion from the nozzle 27 via the exhaust ports 83. As described previously, additional high pressure fuel flows within the interior passage 127 of the waveguide 121 between the waveguide and the valve needle 53.

Figure 10:
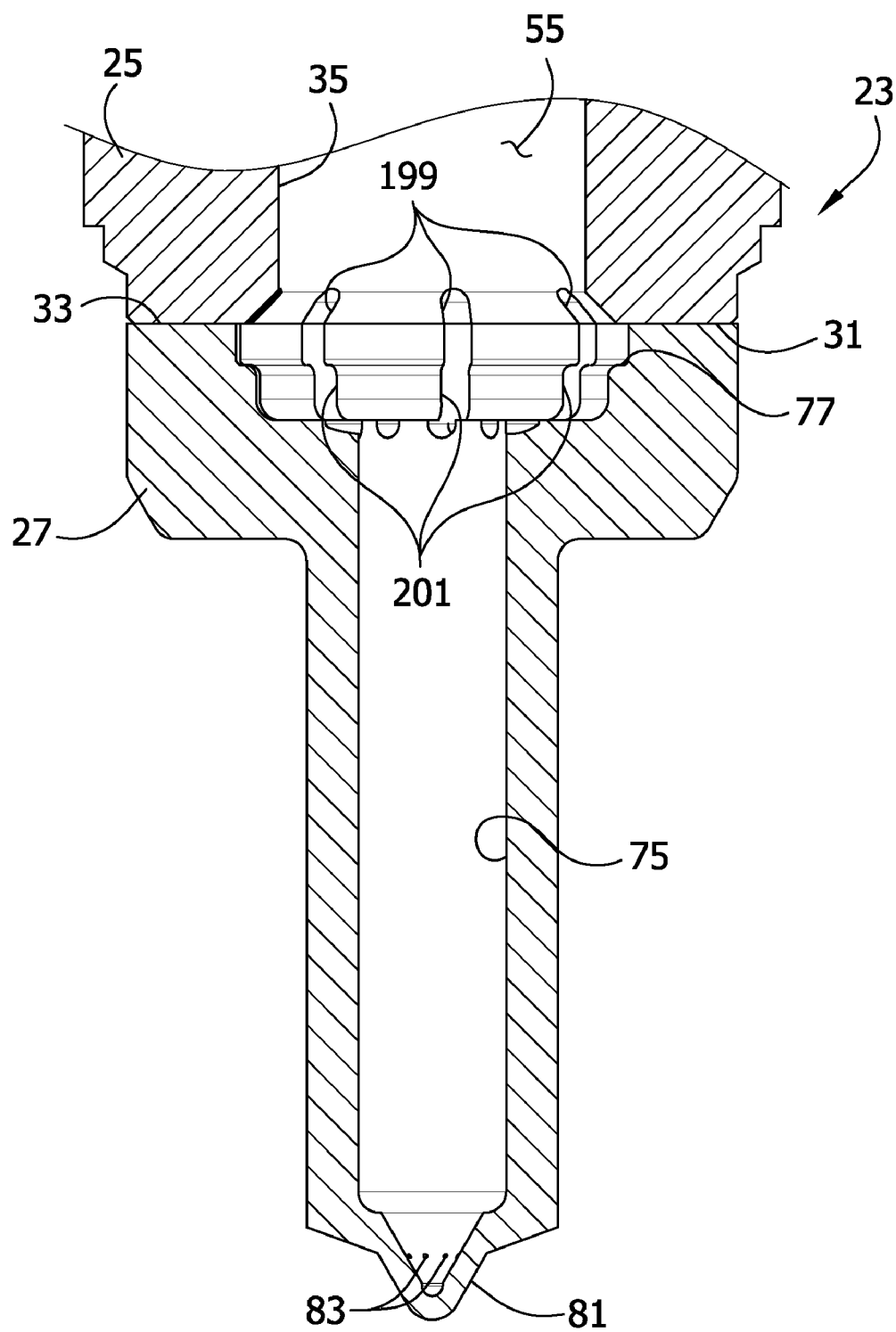
FIG. 10 is a fragmented cross-section of a portion of a fuel injector housing of the fuel injector of FIG. 1, with internal components of the fuel injector omitted to reveal construction of the housing.

Because the mounting member 79 extends transverse to the waveguide 121 within the high pressure chamber 55, the lower end 31 of the main body 25 and the upper end 33 of the nozzle 27 are suitably configured to allow the fuel flow path to divert generally around the mounting member as fuel flows within the high pressure chamber. For example, as best illustrated in FIG. 10, suitable channels 199 are formed in the lower end 31 of the main body 25 in fluid communication with the flow path upstream of the mounting member 79 and are aligned with respective channels 201 formed in the upper end 33 of the nozzle 27 in fluid communication with the flow path downstream of the mounting member. Accordingly, high pressure fuel flowing from the fuel inlet 57 down along the flow path upstream of the mounting member 79 (e.g., between the main body 25 and the sleeve 155/collar 151/ piezoelectric rings 147) is routed through the channels 199 in the main body around the mounting member and through the channels 201 in the nozzle 27 to the flow path downstream of the mounting member (e.g., between the nozzle and the waveguide 121).

In one embodiment, the fuel injector is operated by a suitable control system (not shown) to control operation of the solenoid valve and operation of the excitation device 145. Such control systems are known to those skilled in the art and need not be described further herein except to the extent necessary. Unless an injection operation is occurring, the valve needle 53 is biased by the spring 111 in the bore 35 of the main body 25 to its closed position with the terminal end 115 of the valve needle in sealing contact with the nozzle tip 81 to close the exhaust ports 83. The solenoid valve provides a closure at the recess 95 formed in the head 87 of the pin holder 47 to close the bore 97 that extends longitudinally through the pin holder. No current is supplied by the control system to the waveguide assembly in the closed position of the valve needle 53.

High pressure fuel flows from a source of fuel (not shown) into the fuel injector 21 at the fuel inlet 57 of the housing 23. Suitable fuel delivery systems for delivering pressurized fuel from the fuel source to the fuel injector 21 are known in the art and need not be further described herein. In one embodiment, the high pressure fuel may be delivered to the fuel injector 21 at a pressure in the range of about 8,000 psi (550 bar) to about 30,000 psi (2070 bar). The high pressure fuel flows through the upper distribution channel 59 of the main body 25 to the annular gap 99 between the main body and the pin holder 47, and through the feed channel 101 of the pin holder into the internal channel 91 of the pin holder above the pin 93 and up through the bore 97 in the pin holder. High pressure fuel also flows through the high pressure flow path, i.e., through the lower distribution channel 61 of the main body 25 to the high pressure chamber 55 to fill the high pressure chamber, both outward of the waveguide 121 and within the interior passage 127 of the waveguide. In this condition the high pressure fuel above the pin 93, together with the bias of the spring 111, inhibits the high pressure fuel in the high pressure chamber 55 against urging the valve needle 53 to its open position.

When the injector control system determines that an injection of fuel to the combustion engine is needed, the solenoid valve is energized by the control system to open the pin holder bore 97 so that high pressure fuel flows out from the pin holder to the fuel return channel 71 at the upper end 37 of the main body 25 as lower pressure fuel, thereby decreasing the fuel pressure behind (e.g., above) the pin 93 within the pin holder. Accordingly, the high pressure fuel in the high pressure chamber 55 is now capable of urging the valve needle 53 against the bias of the spring 111 to the open position of the valve needle. In the open position of the valve needle 53, the terminal end 115 of the valve needle is sufficiently spaced from the nozzle tip 81 at the exhaust ports 83 to permit fuel in the high pressure chamber 55 to be exhausted through the exhaust ports.

Upon energizing the solenoid valve to allow the valve needle 53 to move to its open position, such as approximately concurrently therewith, the control system also directs the high frequency electrical current generator to deliver current to the excitation device 145, i.e., the piezoelectric rings 147 in the illustrated embodiment, via the contact ring 165 and suitable wiring 183 that electrically connects the contact ring to the piezoelectric rings. As described previously, the piezoelectric rings 147 are caused to expand and contract (particularly in the longitudinal direction of the fuel injector 21) generally at the ultrasonic frequency at which current is delivered to the excitation device 145.

Expansion and contraction of the rings 147 causes the upper segment 131 of the waveguide 121 to elongate and contract ultrasonically (e.g., generally at the same frequency that the piezoelectric rings expand and contract). Elongation and contraction of the upper segment 131 of the waveguide 121 in this manner excites the waveguide (e.g., suitably at the resonant frequency of the waveguide), and in particular along the lower segment 133 of the waveguide, resulting in ultrasonic vibration of the waveguide along the lower segment and in particular at the expanded portion 195 of the lower segment at the terminal end 123 thereof.

With the valve needle 53 in its open position, high pressure fuel in the high pressure chamber 55 flows along the flow path, and in particular past the ultrasonically vibrating terminal end 123 of the waveguide 121, to the exhaust ports 83 of the nozzle tip 81. Ultrasonic energy is applied by the terminal end 123 of the waveguide 121 to the high pressure fuel just upstream (along the flow path) of the exhaust ports 83 to generally atomize the fuel (e.g., to decrease droplet size and narrow the droplet size distribution of the fuel exiting the injector 21). Ultrasonic energization of the fuel before it exits the exhaust ports 83 produces a pulsating, generally cone-shaped spray of atomized liquid fuel delivered into the combustion chamber served by the fuel injector 21.

In the illustrated embodiment of FIGS. 1-10 and as described previously herein, operation of the pin 93, and hence the valve needle 53, is controlled by the solenoid valve (not shown). It is understood, however, that other devices, such as, without limitation, cam actuated devices, piezoelectric or magnetostrictive operated devices, hydraulically operated devices or other suitable mechanical devices, with or without fluid amplifying valves, may be used to control operation of the valve needle without departing from the scope of this invention.

Figure 11:
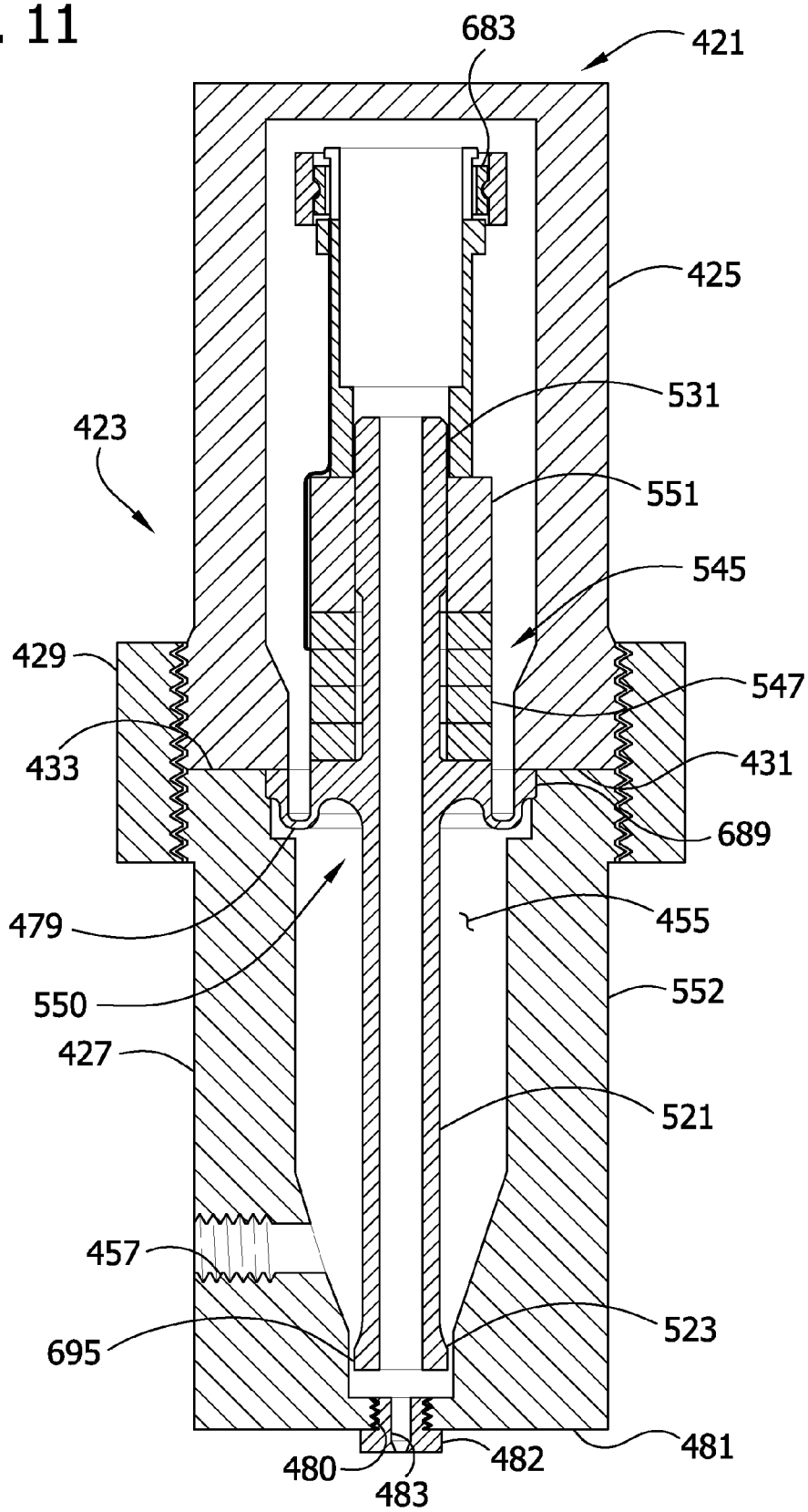
FIG. 11 is a longitudinal cross-section of an ultrasonic liquid delivery device according to a second embodiment of the present invention.

FIG. 11 illustrates a second embodiment of an ultrasonic liquid delivery device, generally indicated at 421, of the present invention. The device 421 of this second embodiment is broadly described herein with reference to any ultrasonically driven device in which a pressurized spray of liquid is exhausted from the device following application of ultrasonic energy to the liquid, it being contemplated that such a device may have application in apparatus such as, without limitation, nebulizers and other drug delivery devices, molding equipment, humidifiers, fuel injection apparatus for engines, paint spray systems, ink delivery systems, mixing systems, homogenization systems, spray drying systems, cooling systems and other applications in which an ultrasonically generated spray of liquid is utilized.

The illustrated device 421 comprises a housing, designated generally at 423, having an inlet 457 for receiving liquid into the housing. The liquid is suitably pressurized in the range of slightly above 0.0 psi (0.0 bar) to about 50,000 psi (3,450 bar). In the illustrated embodiment, the housing 423 is comprised at least in part of an upper (with respect to the vertical orientation of the device 421 illustrated in FIG. 11) housing member 425 and a lower housing member. A lower end 431 of the upper housing member 425 seats against an upper end 433 of the lower housing member 427 and the housing members are secured together by a suitable threaded connector 429. The upper and lower housing members 425, 427 together define an internal chamber 455, in fluid communication with the inlet 457. The lower housing member 427 has a axially extending threaded bore 480 formed in its bottom for threadably receiving an insert 482 therein such that the insert further defines the housing 423 of the device 421. An exhaust port 483 extends axially through the insert 482 to broadly define an exhaust port of the housing 423 through which liquid is exhausted from the housing.

While the insert 482 illustrated in FIG. 11 has a single exhaust port 483, it is contemplated that the insert may comprise more than one exhaust port. It is also contemplated that the insert 482 may be omitted altogether and the bottom of the lower housing member 427 generally closed with one or more exhaust ports formed therein. The housing 423 of the illustrated embodiment is generally cylindrical but may suitably be of any shape, and may be sized depending at least in part on the desired amount of liquid to be disposed within the housing prior to delivery, the number and size of the exhaust ports, and the operating frequency at which the device operates. It is also contemplated that the lower housing member 427 may be configured similar to the nozzle 27 of the embodiment of FIGS. 1-10 with one or more exhaust ports 83 formed in a tip 81 of the nozzle.

The liquid inlet 457 extends transversely through the sidewall 552 of the lower housing member 427 into fluid communication with the internal chamber 455 of the housing 423. It is contemplated, however, that the liquid inlet 457 may be disposed substantially anywhere along the side of the lower housing member 427, or along the side of the upper housing member 425, or even extend axially through the top of the upper housing member and remain within the scope of this invention. Thus, the internal chamber 455 illustrated in FIG. 11 broadly defines a liquid flow path along which liquid flows within the housing 423 to the exhaust port 483 for exhausting the liquid from the housing.

The device 423 illustrated in FIG. 11 lacks a valve member (e.g., a valve member similar to the valve needle 53 of the embodiment of FIGS. 1-10) or other component disposed within the housing to the control the flow of liquid to the exhaust port 483. Rather, in this second embodiment the liquid may flow continuously within the internal chamber 455 to the exhaust port 483. It is understood, however, that a suitable control system (not shown) external of the housing 423 may control the flow of liquid to the housing inlet 457 to thereby control the delivery of liquid to the exhaust port 483 without departing from the scope of this invention.

An elongate ultrasonic waveguide assembly, generally indicated at 550, extends axially of the housing 423 (e.g., in the longitudinal or vertical direction of the housing illustrated in FIG. 11) and is disposed entirely within the internal chamber 455 of the housing. In particular, the waveguide assembly 550 may suitably be constructed in substantially the same manner as the waveguide assembly 150 of the fuel injector 21 of the embodiment of FIGS. 1-10. The terminal end 523 of the waveguide 521 of the assembly 550 is suitably disposed proximate to the exhaust port 483. The term "proximate" is used here in a qualitative sense only to mean that ultrasonic energy is imparted by the terminal end 523 of the waveguide 521 to liquid in the internal chamber 455 just prior to the liquid entering the exhaust port 483, and is not intended to refer to a specific spacing between the exhaust port and the terminal end of the waveguide.

As illustrated in FIG. 11, the inner cross-sectional dimension of the sidewall 552 of the lower housing member 427 decreases toward the lower end 481 of the lower housing member. The enlarged portion 695 at and/or adjacent to the terminal end 523 of the waveguide 521 is thus in closely spaced or even sliding contact relationship with the sidewall 552 toward the lower end 481 of the lower housing member 427, e.g., just upstream (relative to the direction in which pressurized liquid flows within the internal chamber 455 to the exhaust port 483) of the exhaust port so that the flow path of the liquid within the housing narrows at and/or adjacent the terminal end of the waveguide.

It is understood, however, that the terminal end 523 of the waveguide 521 (or other segment thereof) need not be in closely spaced relationship with the sidewall 552 of the lower housing member 427 to remain within the scope of this invention. For example, the outer cross-sectional dimension of the waveguide 521 may be substantially uniform along its length instead of having the enlarged portion 695, or it may narrow toward the terminal end 523 of the waveguide. Alternatively, or additionally, the inner cross-sectional dimension of the sidewall 552 of the lower housing member 427 may not decrease toward the lower end 481 of the lower housing member.

The waveguide 521 is suitably interconnected to the housing 423 within the internal chamber 455 by a transversely extending mounting member 479 constructed substantially similar to the mounting member 79 of the embodiment of FIGS. 1-10. Accordingly, the mounting member 479 vibrationally isolates the housing 423 from mechanical vibration of the waveguide 521. The outer segment 689 of the mounting member 479 is secured between the lower end 431 of the upper housing member 425 and the upper end 433 of the lower housing member 427. Suitable ports (not shown but similar to the ports 199, 201 illustrated in the embodiment of FIGS. 1-10) may be formed in the upper and lower housing members 425, 427 where the outer segment 689 of the mounting member 479 is secured therebetween to permit liquid to flow longitudinally within the internal chamber past the mounting member.

The waveguide assembly 550 also comprises the excitation device 545 (e.g., the piezoelectric rings 547 in the illustrated embodiment), which is compressed against the mounting member 479 by the collar 551 threadably fastened to the upper segment 531 of the waveguide 521. Electrical current is supplied to the excitation device 545 by suitably wiring (not shown but similar to the wiring 181, 183 of the embodiment of FIGS. 1-10) extending through the side of the housing 423 and electrically connected to the contact ring 683 within the internal chamber 455.

In operation, liquid is delivered to the liquid inlet 457 of the housing 423 for flow along the flow path, e.g., within the internal chamber 455, to the exhaust port 483. As pressurized liquid flows past the terminal end 523 of the waveguide 521 to the exhaust port 483, the waveguide assembly 450 is operated in substantially the same manner as the waveguide assembly 150 of the fuel injector 21 of FIGS. 1-10 to ultrasonically vibrate the terminal end of the waveguide, such as in the manner of an ultrasonic horn. Ultrasonic energy is thus imparted by the terminal end 523 of the waveguide 521 to the liquid just prior to the liquid entering the exhaust port 483 to generally atomize the liquid (e.g., to decrease droplet size and narrow the droplet size distribution of the liquid exiting the device 421). Ultrasonic energization of the liquid before it exits the exhaust port 483 generally produces a pulsating, generally cone-shaped spray of atomized liquid delivered from the device 421.

Figure 12:
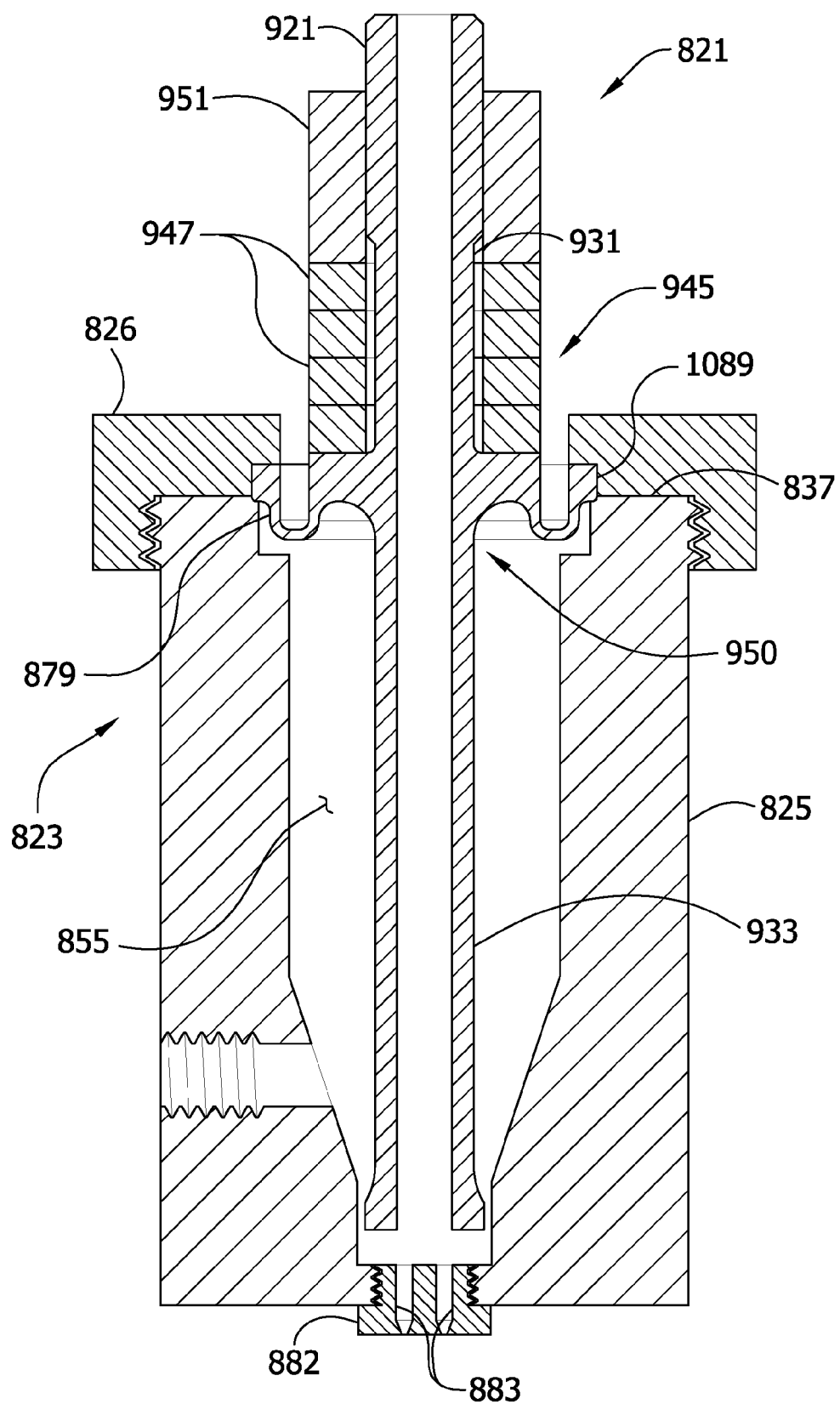
FIG. 12 is a longitudinal cross-section of an ultrasonic liquid delivery device according to a third embodiment of the present invention.

FIG. 12 illustrates an ultrasonic liquid delivery device, generally indicated at 821, according to a third embodiment of the present invention. The device 821 of this third embodiment is similar to that of the second embodiment except that the waveguide assembly 950 of the this third embodiment is illustrated as being only partially disposed within the internal chamber 855 of the housing 823. The housing 823 of this third embodiment comprises a housing member 825 defining the internal chamber 855, and a closure 826 (e.g., an annular closure in the illustrated embodiment) threadably fastened over an open upper end 837 of the housing member to further define the housing and to secure the outer segment 1089 of the mounting member 879 between the closure and the housing member to thereby secure the mounting member (and hence the waveguide assembly 850) in place. The mounting member 879 thus vibrationally isolates the housing 823 from mechanical vibration of the waveguide 921 as described previously in connection with the first and second embodiments. The insert 882 of this third embodiment is illustrated as having a plurality of exhaust ports 883.

In the embodiment illustrated in FIG. 12, the lower segment 933 of the waveguide 921 extends entirely within the internal chamber 855 while the upper segment 931 of the waveguide extends up from the mounting member 879 axially outward of the housing 823. The excitation device 945, e.g., the piezoelectric rings 947, are accordingly disposed exterior of the housing 823 along with the collar 951 that compresses the rings against the upper surface of the mounting member 879. Electrical current may be delivered to the excitation device 945 by suitable wiring (not shown) without the need for the sleeve 155, contact ring 165 and guide ring 167 associated with the fuel injector 21 illustrated in FIGS. 1-10. However, it is understood that such a sleeve, contact ring and guide ring may be incorporated into the device 821 illustrated in FIG. 12 without departing from the scope of this invention.

Figure 13:
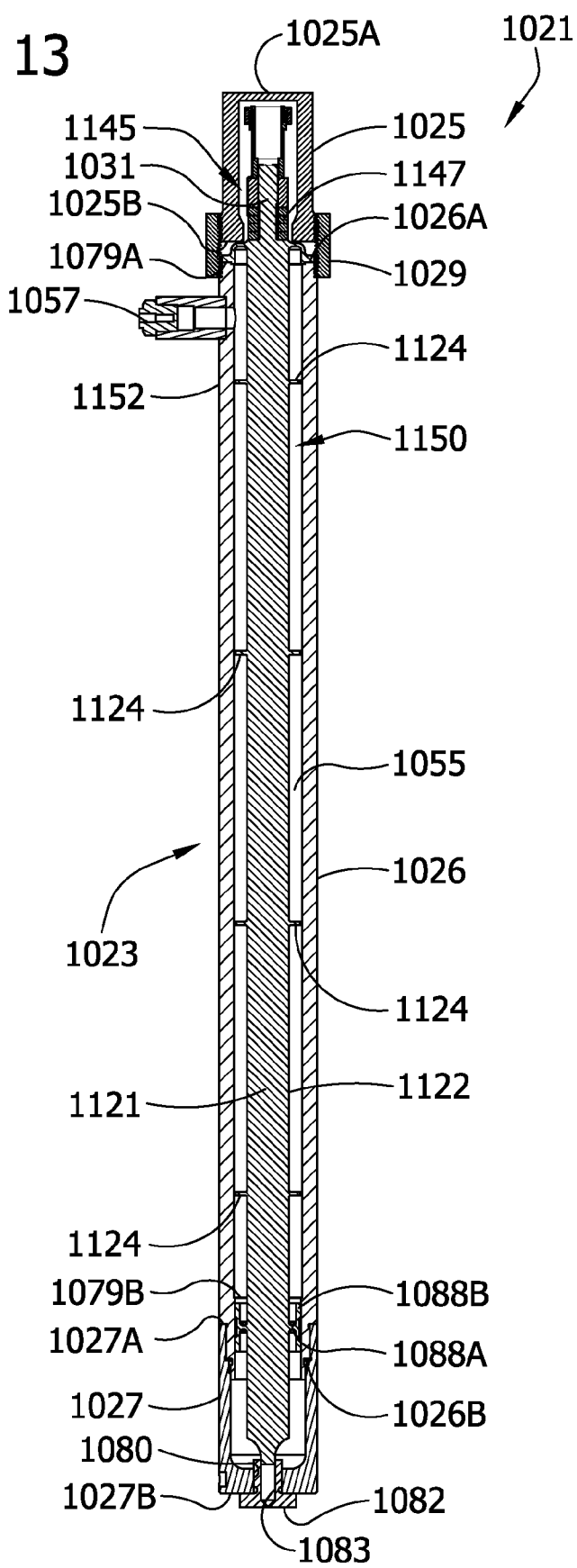
FIG. 13 is a longitudinal cross-section of an ultrasonic liquid delivery device according to a fourth embodiment of the present invention.

FIG. 13 illustrates a fourth embodiment of an ultrasonic liquid delivery device, generally indicated at 1021. The device 1021 of this fourth embodiment is broadly described herein with reference to any ultrasonically driven device in which a pressurized spray of liquid is exhausted from the device following application of ultrasonic energy to the liquid, it being contemplated that such a device may have application in apparatus such as, without limitation, nebulizers and other drug delivery devices, molding equipment, humidifiers, fuel injection apparatus for engines, paint spray systems, ink delivery systems, mixing systems, homogenization systems, spray drying systems, cooling systems and other applications in which an ultrasonically generated spray of liquid is utilized.

The illustrated device 1021 comprises an elongate housing, designated generally at 1023, having an upper housing member 1025 (with respect to the vertical orientation of the device illustrated in FIG. 13), an intermediate housing member 1026, and a lower housing member 1027. The upper housing member 1025 includes a closed upper end 1025A and an open lower end 1025B. The intermediate housing member 1026 is open at its longitudinal ends 1026A, 1026B. The lower housing member 1027 includes an open upper end 1027A and a lower end 1027B. The lower end 1025B of the upper housing member 1025 seats against the upper end 1026A of the intermediate housing member 1026 and the housing members are secured together by a suitable threaded connector 1029. The lower end 1026B of the intermediate housing member 1026 connects (e.g., a threaded connection, snap-fit, or other suitable connection) to the upper end 1027A of the lower housing member 1027. As a result, the upper, intermediate, and lower housing members 1025, 1026, 1027 together define an internal chamber 1055 of the housing 1023. It is contemplated that the housing may alternatively be constructed of less than three pieces, or more than three pieces, within the scope of this invention.

In the embodiment of the device 1021 illustrated in FIG. 13, the intermediate housing member 1026 has a length that is significantly greater than the lengths of the upper and lower housing members 1025, 1027. It is understood, however, that the relative lengths of each of these housing members can vary. For example, the upper, intermediate, and lower housing members 1025, 1026, 1027 can be equal in length, the upper member can have a length greater than the intermediate and lower housing members, or the lower housing member can have a length greater than the upper and intermediate housing members.

An opening 1057 in a sidewall 1152 of the intermediate housing member 1026 adjacent its upper end 1026A defines an inlet 1057 for receiving liquid into the internal chamber 1055 of the housing 1023. It is contemplated, however, that the inlet 1057 may be disposed substantially anywhere along the side of the lower housing member 1027, along the side of the intermediate housing member 1026, or along the side of the upper housing member 1025, or extend through the closed end 1025A of the upper housing member and remain within the scope of this invention.

The lower end 1027B of the lower housing member 1027 has an axially extending threaded bore 1080 for threadably receiving an insert 1082 therein such that the insert further defines the housing 1023 of the device 1021. An exhaust port 1083 extends axially through the insert 1082 to broadly define an exhaust port (or outlet) of the housing 1023 through which liquid is exhausted from the housing. While the insert 1082 illustrated in FIG. 13 has a single exhaust port 1083, it is contemplated that the insert may comprise more than one exhaust port. It is also contemplated that the insert 1082 may be omitted altogether and the lower end 1027B of the lower housing member 1027 may be formed with one or more exhaust ports 1083 therein.

The internal chamber 1055 of the housing 1023 broadly defines a liquid flow path along which liquid can flow within the housing 1023 from the inlet 1057 to the exhaust port 1083 for exhausting the liquid from the internal chamber of the housing. While the device 1021 illustrated in FIG. 13 has a single inlet 1057 and a single exhaust port 1083, it is contemplated that the device may comprise more than one inlet and/or more than one exhaust port. The housing 1023 of the illustrated embodiment is generally cylindrical but may suitably be of any shape, and may be sized depending at least in part on the desired amount of liquid to be disposed within the housing prior to delivery, the number and size of the inlets and exhaust ports, and the operating frequency at which the device operates.

An elongate ultrasonic waveguide assembly, generally indicated at 1150, extends axially of the housing 1123 (e.g., in the longitudinal or vertical direction of the housing illustrated in FIG. 13). The ultrasonic waveguide assembly comprises an ultrasonic waveguide 1121 and an excitation device 1145 held in assembly in the manner described previously in connection with the embodiment of FIGS. 1-10. As illustrated in FIG. 13, at least a portion of the waveguide 1121 is disposed with the internal chamber 1055 of the housing 1023 and, more specifically, in the liquid flow path from the inlet to the exhaust port so that liquid flowing from the inlet 1057 to the exhaust port 1083 is in direct fluid contact with the waveguide.

In one suitable embodiment, the entire ultrasonic waveguide assembly 1150 is disposed within the internal chamber 1055 of the housing 1023. In one arrangement, as illustrated in FIG. 13, the excitation device 1145 is disposed within the internal chamber 1055 but is isolated from the liquid flow path. As a result, liquid passing through the internal chamber 1055 of the housing 1023 does not contact the excitation device 1145. It is understood, however, that the excitation device 1145 can be within the liquid flow path, e.g., if the inlet 1057 is located in the upper end 1025A of the upper housing member 1025.

The ultrasonic waveguide 1121 of this embodiment comprises an elongate, generally cylindrical body having an outer surface 1122. The ultrasonic waveguide 1121 suitably includes a plurality of axially aligned one-half wavelength segments so that the waveguide has one or more nodal regions and two or more antinodal regions. The illustrated waveguide 1121, for example, has five one-half wavelength segments defining five nodal regions and six antinodal regions. It is contemplated, however, that the ultrasonic waveguide 1121 may have more or fewer one-half wavelength segments than five including a single one-half wavelength segment. A single one-half wavelength segment would have one nodal region and two antinodal regions. In one embodiment, the one-half wavelength segments are formed separate from each other and connected end-to-end (e.g., by threaded connection or other suitable connection) to form the waveguide. It is understood, though, that the waveguide may be of single piece construction without departing from the scope of this invention.

As used herein, the "antinodal region" of the ultrasonic waveguide 1121 refers to a longitudinal region or segment of the ultrasonic waveguide along which little (or no) transverse displacement occurs during ultrasonic vibration of the ultrasonic waveguide and longitudinal (e.g., axial in the illustrated embodiment) displacement of the ultrasonic waveguide is generally maximized. In the illustrated embodiment, the ultrasonic waveguide 1121 is such that the antinodal region is particularly defined by an antinodal plane (i.e., a plane transverse to the ultrasonic waveguide at which no transverse displacement occurs while longitudinal displacement is generally maximized) is present. This plane is also sometimes referred to as an antinodal point.

The excitation device 1145 (e.g., the piezoelectric rings 1147 in the illustrated embodiment), is in direct contact with an upper segment 1031 of the ultrasonic waveguide 1121. Electrical current is supplied to the excitation device 1145 by suitable wiring (not shown but similar to the wiring 181, 183 of the embodiment of FIGS. 1-10) extending through the side of the housing 1023 and electrically connected to a contact ring (similar to the contact ring 165 of the embodiment of FIGS. 1-10) within the internal chamber 1055.

As illustrated in FIG. 13, at least one agitating member 1124 extends at least in part transversely outward from the outer surface 1122 of the ultrasonic waveguide 1121. In the illustrated embodiment, a plurality of agitating members 1124 is illustrated in the form of four washer-shaped rings that extend continuously about the circumference of the ultrasonic waveguide 1121 in longitudinally spaced relationship with each other and transversely (e.g., radially in the illustrated embodiment) outward from the outer surface 1122 of the ultrasonic waveguide. In this manner, the vibrational displacement of each of the rings relative to the ultrasonic waveguide 1121 is relatively uniform about the circumference of the ultrasonic waveguide. Each of the agitating members 1124 is disposed in the internal chamber 1055 of the housing 1023 and specifically within the liquid flow path between the inlet 1057 and the exhaust port 1083. As a result, liquid flowing through the flow path from the inlet 1057 to the exhaust port 1083 passes each of the agitating members 1124.

It is understood, however, that the agitating members 1124 need not each be continuous about the circumference of the ultrasonic waveguide 1122. For example, the agitating members 1124 may instead be in the form of spokes, blades, fins or other discrete structural members that extend transversely outward from the outer surface 1122 of the ultrasonic waveguide 1122. It is understood that the number of agitating members 1124 (e.g., the rings in the illustrated embodiment) may be less than or more than four without departing from the scope of this invention. It is also understood that the longitudinal spacing between the agitating members 1124 may be other than as illustrated in FIG. 13 (e.g., either closer or spaced further apart). While the agitating members 1124 illustrated in FIG. 13 are equally longitudinally spaced from each other, it is contemplated that where more than two agitating members are present the spacing between longitudinally consecutive agitating members need not be uniform to remain within the scope of this invention.

The locations of the agitating members 1124 on the ultrasonic waveguide 1121 are at least in part a function of the intended vibratory displacement of the agitating members upon vibration of the ultrasonic waveguide. In one suitable embodiment, each of the agitating members 1124 is positioned at a respective antinodal region of the ultrasonic waveguide 1121 to maximize longitudinal movement of the agitating members along the flow path while minimizing their transverse movement. It is understood that the agitating members 1124 can be spaced from the antinodal region of the ultrasonic waveguide 1121 without departing from the scope of this invention. It is further understood that for embodiments that include two or more agitating members 1124, agitating members 1124 may be located at both an antinodal region and a nodal region of the ultrasonic waveguide.

The agitating members 1124 are sufficiently constructed (e.g., in material and/or dimension such as thickness and transverse length, which is the distance that the agitating member extends transversely outward from the outer surface 1122 of the ultrasonic waveguide 1121) to facilitate dynamic motion, and in particular dynamic flexing/bending of the agitating members 1124 in response to the ultrasonic vibration of the ultrasonic waveguide. While the agitating members 1124 (e.g., the rings) illustrated in FIG. 13 are relatively flat, i.e., relatively rectangular in cross-section, it is understood that the rings may have a cross-section that is other than rectangular without departing from the scope of this invention. The term cross-section is used in this instance to refer to a cross-section taken along one transverse direction (e.g., radially in the illustrated embodiment) relative to the outer surface 1122 of the ultrasonic waveguide 1121). Additionally, although the agitating members 1124 (e.g., the rings) illustrated in FIG. 13 are constructed only to have a transverse component, it is contemplated that one or more of the agitating members may have at least one longitudinal (e.g., axial) component to take advantage of transverse vibrational displacement of the ultrasonic waveguide 1121 (e.g., at and near the nodal region of the ultrasonic waveguide illustrated in FIG. 13) during ultrasonic vibration of the ultrasonic waveguide assembly 1150. For example, one or more of the agitating members 1124 can be formed with a generally T-shaped cross-section, a L-shaped cross-section, a plus-shaped cross-section, or other suitable cross-section.

The waveguide assembly 1150 is suitably interconnected to the housing 1023 within the internal chamber 1055 by a transversely extending mounting member 1079A (broadly, "a first isolating member") constructed substantially similar to the mounting member 79 of the embodiment of FIGS. 1-10. The mounting member vibrationally isolates the housing 1023 from mechanical vibration of the waveguide 1121. It is understood that more than one mounting member can be provided. As illustrated in FIG. 13, the mounting member 1079A is formed as one-piece with the waveguide assembly 1150 but it is contemplated that the mounting member can be formed as a separate piece.

In the illustrated embodiment, the mounting member 1079A is affixed to the housing 1023 at the junction of the upper and intermediate housing members 1025, 1026, which is aligned with one of the nodal region of the ultrasonic waveguide 1121. As a result, the mounting member 1079 inhibits transverse movement of the waveguide assembly 1150. It is contemplated that the mounting member 1079A can have different locations along the length of the ultrasonic waveguide 1121 including in the antinodal region without departing from the scope of this invention.

The waveguide assembly 1150 is axially supported within the internal chamber 1055 of the housing 1023 by a stabilizing member 1079B (broadly, "a second isolating member") spaced longitudinally from the mounting member. The stabilizing member 1079B includes a radial component 1088A and an axial component 1088B as described in U.S. Pat. No. 6,676,003, the disclosure of which is incorporated herein by reference to the extent it is consistent herewith. The stabilizing member 1079B cooperates with the mounting member 1079A to vibrationally isolate the housing 1023 from mechanical vibration of the waveguide 1121.

In one suitable embodiment, the stabilizing member 1079B is positioned in the nodal region of the ultrasonic waveguide 1121 to inhibit transverse movement of the waveguide assembly 1150. It is contemplated that the stabilizing member 1079B can have different locations along the length of the ultrasonic waveguide 1121 including in the antinodal region without departing from the scope of this invention. As illustrated in FIG. 13, the stabilizing member 1079B is disposed within the internal chamber 1055 of the housing 1023 intermediate the inlet 1057 and the exhaust port 1083 such that the stabilizing member is disposed within the flow path. As a result, the stabilizing member 1079B includes openings (not shown) for allowing liquid to pass the stabilizing member as it flows from the inlet 1057 to the exhaust port 1083.

The stabilizing member 1079B is sized and shaped relative to the housing 1023 so that it has a friction fit with the housing. More specifically, the radial component 1088A of the stabilizing member 1079B contacts the inner surface of the housing 1023 with sufficient frictional resistance that during dynamic displacement of the ultrasonic waveguide 1121, the radial component 1088A remains stationary with respect to the housing. The axial component 1088B of the stabilizing member 1079B bends/flexes during dynamic displacement of the ultrasonic waveguide 1121 so that the ultrasonic waveguide can move without movement of the radial component 1088A. The stabilizing member 1079B, however, is capable of sliding movement relative to the housing 1023 in the axial (longitudinal) direction so that the ultrasonic waveguide can be inserted into and removed from the internal chamber 1055 of the housing 1023. It is understood that more than one stabilizing members can be provided. As illustrated in FIG. 13, the stabilizing member 1079B is formed as one-piece with the waveguide assembly 1150 but it is contemplated that the stabilizing member can be formed as a separate piece.

In operation, liquid is delivered to the liquid inlet 1057 of the housing 1023 for flow along the flow path, e.g., within the internal chamber 1055, to the exhaust port 1083. As pressurized liquid flows along the waveguide 1121 toward the exhaust port 1083, the waveguide assembly 1050 is operated in substantially the same manner as the waveguide assembly 150 of the fuel injector 21 of FIGS. 1-10 to ultrasonically vibrate the waveguide. Ultrasonic energy is thus imparted by ultrasonic waveguide 1121 to the liquid prior to the liquid exiting the flow path via exhaust port 1083 to generally atomize the liquid (e.g., to decrease droplet size and narrow the droplet size distribution of the liquid exiting the device 1021). Ultrasonic energization of the liquid before it exits the exhaust port 1083 generally produces a pulsating, generally cone-shaped spray of atomized liquid delivered from the device 1021. Moreover, the agitating members 1124 mix the liquid as it flows through the flow path. Certain liquids (e.g., solutions) can unwantingly separate into various phases. The agitating members 1124 agitate the liquid during operation of the ultrasonic waveguide 1121 as the liquid passes the agitating members to thereby maintain the liquid in a mixed state. More specifically, the agitating members 1124 are dynamically displaced longitudinally relative to the housing 1023 within the liquid flow path due to their placement within the antinodal region of the ultrasonic waveguide 1121.

Figure 14:
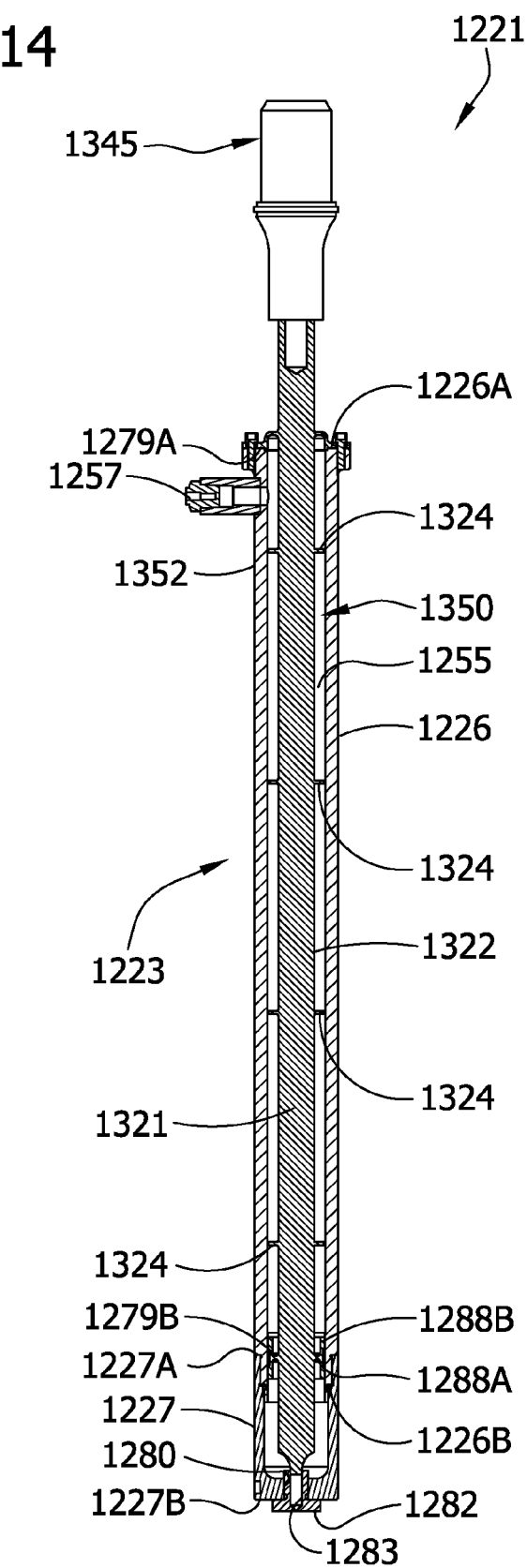
FIG. 14 is a longitudinal cross-section of an ultrasonic liquid delivery device according to a fifth embodiment of the present invention.

FIG. 14 illustrates an ultrasonic liquid delivery device, generally indicated at 1221, according to a fifth embodiment of the present invention. The device 1221 of this fifth embodiment is similar to that of the fourth embodiment except that a waveguide assembly 1350 of this fifth embodiment is illustrated as being only partially disposed within an internal chamber 1255 of a housing 1223. The housing 1223 of this fifth embodiment comprises an internal chamber 1255, and a closure (e.g., a first mounting member 1279A in the illustrated embodiment) closing an open, upper end 1226A of an upper housing member 1226 to further define the internal chamber. In the embodiment illustrated of FIG. 14, a lower segment of the ultrasonic waveguide 1321 extends entirely within the internal chamber 1255 while an upper segment of the ultrasonic waveguide extends up from the first mounting member 1279A axially outward of the housing 1223. An excitation device 1345 is accordingly disposed exterior of the housing 1223. Electrical current may be delivered to the excitation device 1345 by suitable wiring (not shown) without the need for the sleeve, contact ring and guide ring associated with the fuel injector 21 illustrated in FIGS. 1-10. However, it is understood that such a sleeve, contact ring and guide ring may be incorporated into the device 1221 illustrated in FIG. 14 without departing from the scope of this invention. The embodiment illustrated in FIG. 14 is well suited for uses having liquid that is too hot for the excitation device 1345. Not only does this embodiment isolate the excitation device 1345 from the liquid passing through the internal chamber 1255 of the housing 1223 but also allows for cooling air to be supplied to the excitation device to maintain the excitation device within an acceptable range.

When introducing elements of the present invention or preferred embodiments thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions and methods without departing from the scope of the invention, it is intended that all matter contained in the above description and shown in the accompanying drawings shall be interpreted as illustrative and not in a limiting sense.

What is claimed is:

1. An ultrasonic liquid delivery device comprising:

an elongate housing having an internal chamber, an inlet in fluid communication with the internal chamber of the housing whereby liquid enters the internal chamber, and an outlet in fluid communication with the internal chamber of the housing whereby liquid within the chamber exits the housing;

an elongate ultrasonic waveguide disposed at least in part within the internal chamber of the housing to ultrasonically energize liquid within the internal chamber prior to said liquid being exhausted from the housing through the outlet, the ultrasonic waveguide having an agitating member extending outward from the ultrasonic waveguide within the internal chamber of the housing intermediate the inlet and the outlet, the agitating member and the ultrasonic waveguide being constructed and arranged for dynamic motion of the agitating member relative to the ultrasonic waveguide upon ultrasonic vibration of the ultrasonic waveguide, wherein the agitating member and the ultrasonic waveguide are constructed and arranged to amplify the displacement of the agitating member relative to the displacement of the ultrasonic waveguide upon ultrasonic vibration of the ultrasonic waveguide, and wherein the ultrasonic waveguide has a nodal region and an antinodal region, the agitating member extending transversely outward from the ultrasonic waveguide in the antinodal region; and an excitation device operable to ultrasonically excite said ultrasonic waveguide and the agitating member.

2. The liquid delivery device set forth in claim 1 wherein a plurality of agitating members extend outward from the ultrasonic waveguide in longitudinally spaced relationship with each other within the internal chamber of the housing.

3. The liquid delivery device set forth in claim 1 wherein the agitating member comprises a ring extending circumferentially around the ultrasonic waveguide.

4. The liquid delivery device set forth in claim 2 wherein at least one of the plurality of agitating members extends transversely outward from the ultrasonic waveguide in the nodal region.

5. The liquid delivery device set forth in claim 4 wherein the at least one of the plurality of agitating members has a generally T-shaped cross-section.

6. The liquid delivery device set forth in claim 1 wherein a length of the ultrasonic waveguide defines at least one half wavelength segments.

7. The liquid delivery device set forth in claim 6 wherein the length of the ultrasonic waveguide defines at least three half wavelength segments, at least one agitating member extending outward from at least two of the half wavelength segments.

8. The liquid delivery device set forth in claim 1 wherein the ultrasonic waveguide and the agitating member are formed as a single-piece.

9. The liquid delivery device set forth in claim 1 wherein the entire ultrasonic waveguide is disposed within the internal chamber of the housing.

10. The liquid delivery device set forth in claim 9 wherein at least a portion of the excitation device is disposed within the internal chamber of the housing.

11. The liquid delivery device set forth in claim 1 further comprising at least one isolating member for mounting the ultrasonic waveguide within the internal chamber of the housing, the at least one mounting member being constructed to substantially vibrationally isolate the housing from the ultrasonic waveguide.

12. The liquid delivery device set forth in claim 11 wherein the at least one isolating member comprises a mounting member.

13. The liquid delivery device set forth in claim 11 wherein the at least one isolating member comprises a stabilizing member.

14. An ultrasonic liquid delivery device comprising:

a housing having an inlet for receiving liquid into the housing, an outlet through which liquid exits the housing, and an internal flow path in fluid communication with the inlet and the outlet to direct the flow of liquid within the housing from the inlet to the outlet;

an ultrasonic waveguide separate from the housing, said ultrasonic waveguide being elongate and disposed at least in part within the flow path to ultrasonically energize liquid within the flow path prior to said liquid exiting the housing through the outlet, wherein the ultrasonic waveguide has a plurality of nodal regions and a plurality of antinodal regions;

an agitating member extending outward from the ultrasonic waveguide generally at one of said antinodal regions of the waveguide; and an excitation device operable to ultrasonically excite said ultrasonic waveguide and the agitating member.

15. The liquid delivery device set forth in claim 14 wherein a plurality of agitating members extend outward from the ultrasonic waveguide generally at said plurality of antinodal regions of the ultrasonic waveguide.

16. The liquid delivery device set forth in claim 15 wherein the number of antinodal regions of the ultrasonic waveguide is greater than the number of agitating members.

17. The liquid delivery device set forth in claim 16 wherein there are two more antinodal regions of ultrasonic waveguide than there are agitating members.

18. The liquid delivery device set forth in claim 14 wherein the excitation device is held in assembly with the ultrasonic waveguide, the excitation device being in direct contact with the ultrasonic waveguide generally at one of said plurality of antinodal regions.

19. The liquid delivery device set forth in claim 14 further comprising an isolating member for substantially vibrationally isolating the housing from the ultrasonic waveguide.

20. The liquid delivery device set forth in claim 19 wherein the isolating member is operatively connected to the ultrasonic waveguide generally at said nodal region of the ultrasonic waveguide.

21. An ultrasonic liquid delivery device comprising:

an elongate housing having an inlet for receiving liquid into the housing, an outlet through which liquid is exhausted from the housing, and a flow path within the housing in fluid communication with the inlet and the outlet for directing said liquid to flow within the housing from said inlet to said outlet;

an elongate ultrasonic waveguide disposed at least in part within the flow path to ultrasonically energize liquid within the flow path prior to said liquid exiting the housing through the outlet, the ultrasonic waveguide having at least two wavelength segments;

a plurality of agitating members extending transversely outward from the ultrasonic waveguide, the agitating members and the ultrasonic waveguide being constructed and arranged for dynamic motion of the agitating members relative to the ultrasonic waveguide upon ultrasonic vibration of the ultrasonic waveguide; and an excitation device operable to ultrasonically excite said ultrasonic waveguide and the agitating members.

* * * * *